US009504437B2

United States Patent
Noshi et al.

(10) Patent No.: US 9,504,437 B2
(45) Date of Patent: Nov. 29, 2016

(54) DIAGNOSTIC IMAGING APPARATUS AND CONTROL METHOD OF THE SAME

(71) Applicant: Toshiba Medical Systems Corporation, Otawara-shi (JP)

(72) Inventors: Yasuhiro Noshi, Otawara (JP); Manabu Teshigawara, Otawara (JP)

(73) Assignee: TOSHIBA MEDICAL SYSTEMS CORPORATION, Otawara-shi (JP)

( * ) Notice: Subject to any disclaimer, the term of this patent is extended or adjusted under 35 U.S.C. 154(b) by 349 days.

(21) Appl. No.: 14/332,477

(22) Filed: Jul. 16, 2014

(65) Prior Publication Data

US 2014/0328455 A1  Nov. 6, 2014

(30) Foreign Application Priority Data

Jun. 20, 2012  (JP) .................. 2012/139138
Jun. 20, 2012  (JP) .................. 2012/139139

(51) Int. Cl.
*A61B 6/00* (2006.01)
*A61B 6/03* (2006.01)
*A61B 6/04* (2006.01)

(52) U.S. Cl.
CPC .......... *A61B 6/5235* (2013.01); *A61B 6/0457* (2013.01); *A61B 6/4417* (2013.01); *A61B 6/5258* (2013.01); *A61B 6/032* (2013.01); *A61B 6/035* (2013.01); *A61B 6/037* (2013.01)

(58) Field of Classification Search
CPC ...... A61B 6/032; A61B 6/035; A61B 6/037; A61B 6/0457; A61B 6/4417; A61B 6/5235; A61B 6/5258; A61B 6/025; A61B 6/14; A61B 6/4405; A61B 6/4447; A61B 6/4475; A61B 6/504; A61B 6/00; A61B 6/06; A61B 6/08; A61B 6/105; A61B 6/12
USPC .................... 378/4, 20, 16, 8, 205
See application file for complete search history.

(56) References Cited

U.S. PATENT DOCUMENTS 6,914,958 B2 * 7/2005 Ganin .............. A61B 6/032
378/26
2002/0081008 A1    6/2002 Wollenweber
(Continued)

FOREIGN PATENT DOCUMENTS

JP    2002-330960 A    11/2002
JP    2003-310604 A    11/2003
(Continued)

OTHER PUBLICATIONS

International Search Report mailed Aug. 6, 2013 for PCT/JP2013/066882 filed on Jun. 19, 2013 with English Translation.
English translation of the International Preliminary Report on Patentability and Written Opinion issued on Dec. 23, 2014 in PCT/JP2013/066882.

*Primary Examiner* — Irakli Kiknadze
(74) *Attorney, Agent, or Firm* — Oblon, McClelland, Maier & Neustadt, L.L.P.

(57) ABSTRACT

An diagnostic imaging apparatus including: a correction table; a top panel height calculation unit configured to calculate a height of the top panel corresponding to the distance between the fulcrum of the top panel and the imaging position, from an image captured by continuous imaging of the subject; an imaging position estimation unit configured to estimate an imaging position of an image captured by a different imaging method from a method for the captured image based on the height of the top panel calculated by the top panel height calculation unit, the distance between the fulcrum of the top panel corresponding to the height and the imaging position, and the correction table; and an image correction unit configured to align the imaging position of the image captured by the different imaging method with the imaging position of the image captured by the continuous imaging.

12 Claims, 17 Drawing Sheets

(56) References Cited

U.S. PATENT DOCUMENTS

| | | | |
|---|---|---|---|
| 2002/0090058 A1* | 7/2002 | Yasuda | A61B 6/08 378/205 |
| 2006/0184012 A1 | 8/2006 | Marzendorfer | |
| 2006/0269039 A1* | 11/2006 | Raupach | A61B 6/032 378/16 |
| 2012/0243655 A1* | 9/2012 | Ninomiya | A61B 6/027 378/8 |

FOREIGN PATENT DOCUMENTS

| | | |
|---|---|---|
| JP | 2004-180846 A | 7/2004 |
| JP | 2005-291814 A | 10/2005 |
| JP | 2006-175236 A | 7/2006 |
| JP | 2007-167408 A | 7/2007 |
| JP | 2012-045318 A | 3/2012 |
| WO | WO 2012/063957 A1 | 5/2012 |

* cited by examiner

US 9,504,437 B2

DIAGNOSTIC IMAGING APPARATUS AND CONTROL METHOD OF THE SAME

CROSS-REFERENCE TO RELATED APPLICATION

This application is a Continuation Application of No. PCT/JP2013/66882, filed on Jun. 19, 2013, and the PCT application is based upon and claims the benefit of priority from Japanese Patent Application No. 2012-139138, filed on Jun. 20, 2012, and Japanese Patent Application No. 2012-139139, filed on Jun. 20, 2012, the entire contents all of which are incorporated herein by reference.

FIELD

The present invention relates to a diagnostic imaging apparatus and a control method of the same.

BACKGROUND

In recent years, a medical diagnostic imaging apparatus including a plurality of medical diagnostic imaging apparatuses integrated with each other has been in practical use. Specifically, an apparatus including a PET (Positron Emission Tomography) diagnostic apparatus for functional diagnosis of body tissue of a subject, and an X-ray CT (Computed Tomography) apparatus for imaging morphological information of body tissue of a subject integrated with each other (also referred to as a PET-CT apparatus) has been in practical use.

The PET-CT apparatus can continuously conduct a PET examination and an X-ray CT examination. Thus, the PET-CT apparatus can, by itself, generate a PET image and an X-ray CT image to generate a fusion image of the PET image and the X-ray CT image superimposed on each other.

In such a medical diagnostic imaging apparatus, generally, a PET gantry (radiation detection unit) used in the PET diagnostic apparatus, and an X-ray CT gantry (X-ray scanning unit) used in the X-ray CT apparatus are placed close to each other. Such a medical diagnostic imaging apparatus includes a bed having a top panel on which a human subject is placed, and the PET diagnostic apparatus and the X-ray CT apparatus share the bed.

In the medical diagnostic imaging apparatus, the PET gantry in the PET diagnostic apparatus and the X-ray CT gantry in the X-ray CT apparatus are successively arranged in a tandem positional relationship, and the PET gantry and the X-ray CT gantry each have a tunnel portion extending therethrough. The top panel of the bed is inserted into the tunnel portions in the gantries longitudinally of the top panel.

Thus, in the medical diagnostic imaging apparatus, a distance between the bed and the radiation detection unit of the PET diagnostic apparatus is different from a distance between the bed and the X-ray scanning unit of the X-ray CT apparatus, and thus depression of the top panel (also referred to as bending of the top panel) also differs due to a load in an imaging position of each gantry. Thus, various methods for correcting the bending of the top panel have been studied.

In a medical diagnostic imaging apparatus using a plurality of imaging methods, imaging is performed by each imaging method, and thus imaging surfaces shows different positions (imaging positions), and the top panel bends in a different manner in each imaging position. Specifically, even if the PET gantry and the X-ray CT gantry image the same site, bending of the top panel due to a load is different. For the PET diagnostic apparatus, a position of the top panel is not projected on a PET image, and thus when the PET image and the X-ray CT image are superimposed on each other, it is difficult to align the positions of the top panels in the captured images, thereby making it difficult to generate a fusion image with high accuracy of the PET image and the X-ray CT image properly superimposed on each other.

DETAILED DESCRIPTION

A diagnostic imaging apparatus according to this embodiment will be described with reference to the accompanying drawings.

To solve the above-described problems, the present embodiments provide the diagnostic imaging apparatus including: a correction table in which a protrusion amount of a top panel and a bending amount of the top panel corresponding to the protrusion amount are associated, or a distance between a fulcrum of the top panel and an imaging position of a subject, and a height of the top panel in the imaging position are associated; a top panel height calculation unit configured to calculate a height of the top panel corresponding to the distance between the fulcrum of the top panel and the imaging position, from an image captured by continuous imaging of the subject; an imaging position estimation unit configured to estimate an imaging position of an image captured by a different imaging method from a method for the captured image based on the height of the top panel calculated by the top panel height calculation unit, the distance between the fulcrum of the top panel corresponding to the height and the imaging position, and the correction table; and an image correction unit configured to align the imaging position of the image captured by the different imaging method with the imaging position of the image captured by the continuous imaging.

As a result, the diagnostic imaging apparatus according to this embodiment can align an imaging position of an image captured by continuous imaging with an imaging position of an image captured by a different imaging method, thereby allowing correction with high accuracy with fusion of the captured images, and obtaining a fusion image.

First Embodiment

Now, a PET-CT apparatus (diagnostic imaging apparatus) 100 according to a first embodiment will be described with reference to the accompanying drawings. In the first embodiment, a PET-CT apparatus is described as an example of an apparatus including a plurality of medical diagnostic imaging apparatuses using different imaging methods integrated with each other.

Figure 1:
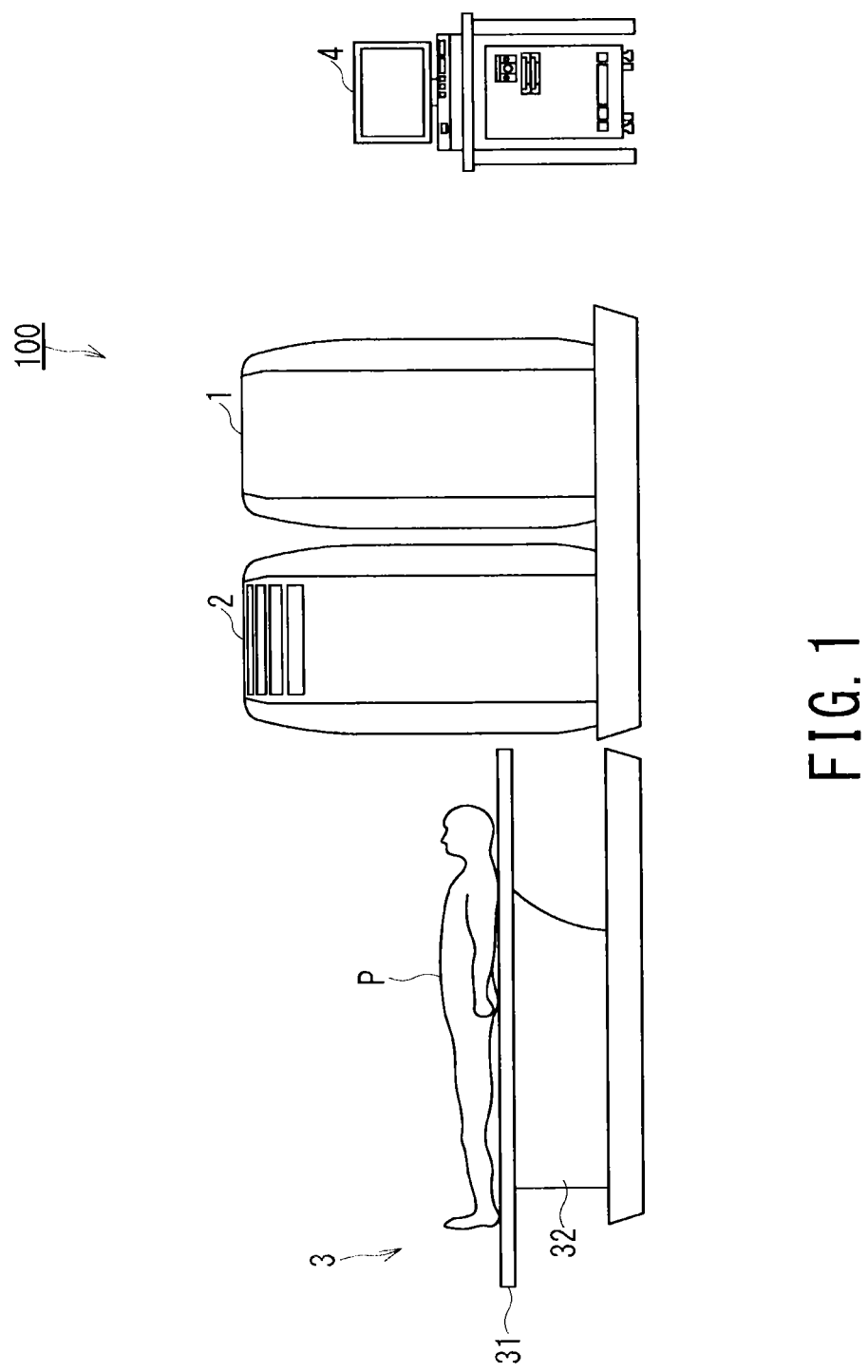
FIG. 1 is a conceptual view showing an exemplary configuration of a PET-CT apparatus according to a first embodiment.

FIG. 1 is a schematic configuration diagram of the PET-CT apparatus 100 according to the first embodiment.

As shown in FIG. 1, the PET-CT apparatus 100 includes a PET frame device 1, a CT frame device 2, a bed device 3, and a console device 4. A radioisotope or a labeled compound thereof is administered to a subject P.

The PET frame device 1 detects a pair of gamma rays emitted from body tissue that incorporates a positron-emitting radionuclide administered to the subject P, and generates projection data of the gamma rays (also referred to as gamma ray projection data) for reconfiguring a PET image. The PET frame device 1 uses a nature of a labeled compound such as a radioisotope being selectively incorporated by a particular tissue or organ in a body, to measure a gamma ray emitted from the isotope outside the body, and image dose distribution of the radioisotope.

The CT frame device 2 applies an X-ray from outside the subject P, detects the X-ray having passed through a tissue or organ of the subject P, and generates X-ray projection data for reconfiguring an X-ray CT image. The CT frame device 2 images a difference in X-ray transmittance between tissues or organs, or measures intensity of the X-ray using a detector to reconfigure an image from a measured value.

The bed device 3 is a bed on which the subject P is placed, and includes a top panel 31, and a bed 32. The bed device 3 is moved to an imaging port of the PET frame device 1 or the CT frame device 2 based on an instruction of an operator of the PET-CT apparatus 100 having received via the console device 4. Specifically, the PET-CT apparatus 100 moves the bed device 3 based on the instruction from the console device 4 to capture an X-ray CT image or a PET image. The movement of the bed device 3 will be described.

Figure 2A:
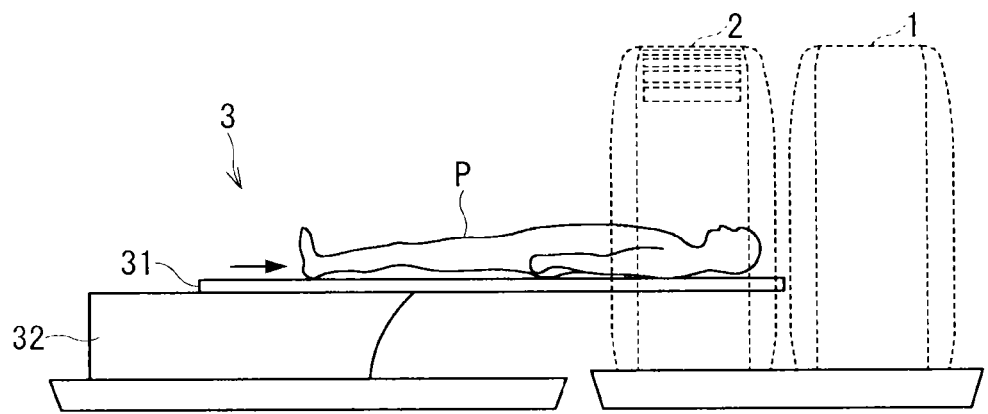
FIGS. 2A and 2B illustrate movement of a bed device according to the first embodiment.
Figure 2B:
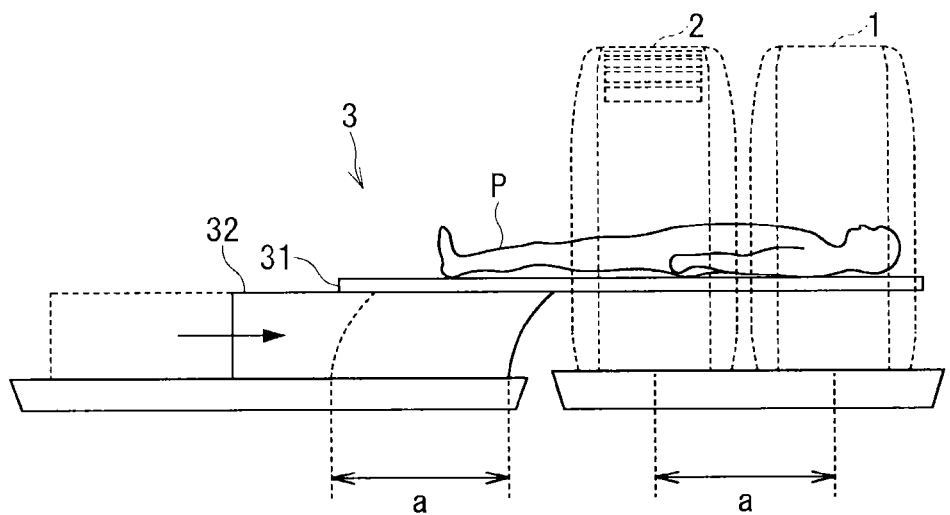

FIGS. 2A and 2B illustrate the movement of the bed device 3 according to the first embodiment.

As shown in FIGS. 2A and 2B, the console device 4 (FIG. 1) uses a drive mechanism (not shown) to move the top panel 31 and the bed 32 along a body axis of the subject P. For example, to capture an X-ray CT image, as shown in FIG. 2A, the PET-CT apparatus 100 horizontally moves the top panel 31 toward the CT frame device 2. Then, the PET-CT apparatus 100 uses a top panel continuous moving method for horizontally moving the top panel 31 to scan an imaging site of the subject P (as an example, there is a helical scanning method for spiral and continuous X-ray scanning). The CT frame device 2 captures an X-ray CT image. The X-ray is a type of electromagnetic waves, and has wavelengths of several hundred angstroms to 0.1 angstroms.

After capturing the X-ray CT image, as shown in FIG. 2B, the PET-CT apparatus 100 horizontally moves the bed 32 along the body axis with the top panel 31 being protruded from the bed 32. Then, the PET-CT apparatus 100 inserts an imaging site of the subject P into the imaging port of the PET frame device 1.

As shown in FIG. 2B, the bed 32 is moved by the same distance as a distance "a" between central positions of detectors in the PET frame device 1 and the CT frame device 2. Specifically, the bed 32 is moved by the distance "a" to provide the same protrusion amount from the bed 32 in imaging the same site of the subject P.

Then, when capturing a PET image, the PET-CT apparatus 100 images a part of the subject P, then horizontally moves the top panel 31 stepwise by a predetermined amount of movement from a stop state of imaging, and further images other portions. As such, the PET frame device 1 in the PET-CT apparatus 100 can image a wide range of the subject P by an imaging method of repeating movement and imaging (also referred to as a step-and-shoot method).

The console device 4 shown in FIG. 1 receives an instruction of an operator and controls an imaging process of the PET-CT apparatus 100. Now, a configuration of the console device 4 will be described.

Figure 3:
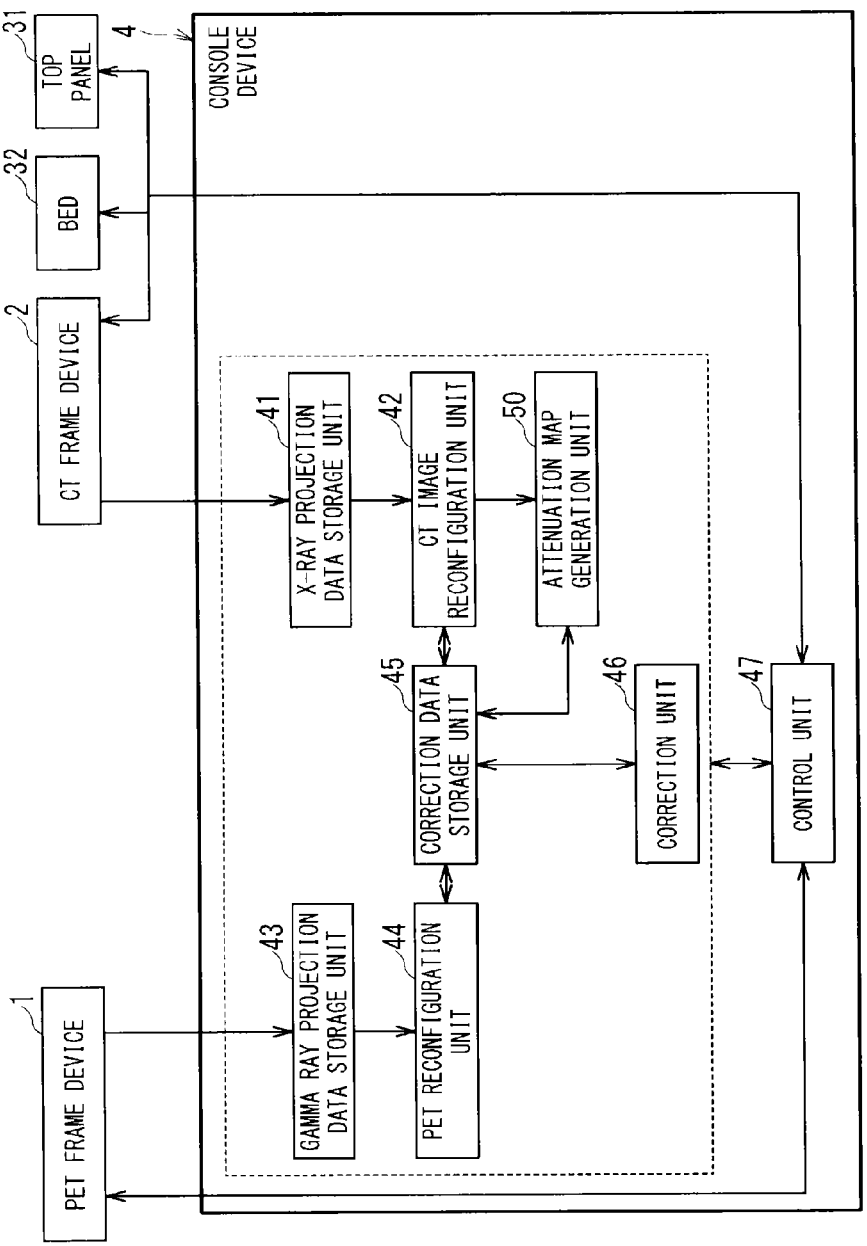
FIG. 3 shows a configuration of a console device according to the first embodiment.

FIG. 3 shows a configuration of the console device 4 according to the first embodiment.

As shown in FIG. 3, the console device 4 includes an X-ray projection data storage unit 41, a CT image reconfiguration unit 42, a gamma ray projection data storage unit 43, a PET reconfiguration unit 44, a correction data storage unit 45, an attenuation map generation unit 50, a correction unit 46, and a control unit 47.

The X-ray projection data storage unit 41 stores X-ray projection data transmitted from the CT frame device 2. Specifically, the X-ray projection data storage unit 41 stores X-ray projection data for reconfiguration of an X-ray CT image.

The CT image reconfiguration unit 42 performs a back projection process of X-ray projection data for reconfiguration stored in the X-ray projection data storage unit 41, for example, by a FBP (Filtered Back Projection) method to reconfigure an X-ray CT image. Specifically, the CT image reconfiguration unit 42 reconfigures, from the X-ray projection data, a plurality of X-ray CT images that are a plurality of sectional images captured perpendicularly to the body axis of the subject P based on imaging conditions (for example, a slice width) determined by an imaging plan in a general examination using the PET-CT apparatus 100.

The gamma ray projection data storage unit 43 stores gamma ray projection data transmitted from the PET frame device 1.

The PET reconfiguration unit 44 reconfigures a PET image from the gamma ray projection data stored in the gamma ray projection data storage unit 43, for example, by a statistical reconfiguration method. The PET reconfiguration unit 44 performs attenuation correction of a PET image using an attenuation map described later.

The correction data storage unit 45 stores the X-ray CT image reconfigured by the CT image reconfiguration unit 42, and the PET image reconfigured by the PET reconfiguration unit 44. The correction data storage unit 45 stores a top panel reference profile indicating a reference position of the top panel 31, and a three-dimensional correction table for estimating a tilt of the top panel 31 in the PET image.

In the first embodiment, as an example of the correction table, for example, an example will be described using a three-dimensional correction table (first correction table) in which a protrusion amount of the top panel 31 from a fulcrum to an imaging position, a bending amount of the top panel 31 corresponding to the protrusion amount, and a tilt of the top panel 31 are associated.

In a second embodiment, as another example of the correction table, for example, an example will be described using a three-dimensional correction table (second correction table) in which a distance between the fulcrum of the top panel 31 and the imaging position of the subject P, a load of the subject P applied to the top panel 31 (for example, body weight), and a height of the top panel 31 in the imaging position are associated.

The attenuation map generation unit 50 uses the X-ray CT image reconfigured by the CT image reconfiguration unit 42 to generate an attenuation map (μMap) for correcting attenuation of a gamma ray generated in a body of the subject P. The attenuation map includes pixel values converted from the X-ray CT image. The attenuation map generation unit 50 corrects the attenuation map so that heights of the top panels in the PET image and the X-ray CT image match based on a top panel sagging correction amount (a correction amount by a top panel sagging correction amount calculation process described later). Then, the attenuation map generation unit 50 stores the corrected attenuation map in the correction data storage unit 45.

The correction unit 46 reads the X-ray CT image or the PET image stored in the correction data storage unit 45, and reads (or refers to) the top panel reference profile or the three-dimensional correction table stored in the correction data storage unit 45, corrects the X-ray CT image and the PET image to generate a fusion image. In particular, the PET reconfiguration unit 44 performs attenuation correction of the PET image, and the correction unit 46 corrects the PET image having subjected to the attenuation correction to a position of the top panel reference profile so as to match the position of the X-ray CT image. Details of the correction unit 46 will be described later.

The control unit 47 controls a general operation of the PET-CT apparatus 100. Specifically, the control unit 47 controls operations of the PET frame device 1, the CT frame device 2, the top panel 31, and the bed 32 to control the imaging process by the PET-CT apparatus 100.

For example, the control unit 47 uses the X-ray projection data for X-ray reconfiguration stored in the X-ray projection data storage unit 41 to control a reconfiguration process by the CT image reconfiguration unit 42. The control unit 47 uses the gamma ray projection data stored in the gamma ray projection data storage unit 43 to control a reconfiguration process by the PET reconfiguration unit 44 or attenuation correction. The control unit 47 controls a top panel sagging correction amount calculation process (described later) by the correction unit 46, and receives an instruction of an operator from an input/output device (not shown) to display a fusion image on a display unit (not shown).

The control unit 47 includes a CPU (Central Processing Unit), a ROM (Read Only Memory), a RAM (Random Access Memory) (not shown), or the like.

The CPU loads various programs stored in the ROM to the RAM to expand the programs and achieve functions of the programs. The RAM is used as a working area (working memory). The ROM stores various programs. The various programs stored in the ROM include programs for achieving the imaging process, the reconfiguration process, and the top panel sagging correction amount calculation process (first correction amount calculation process) by the correction unit 46.

Next, misalignment between an image captured by the step-and-shoot method by the PET frame device 1 and an image captured by the helical scanning method by the CT frame device 2 will be described.

Figure 4:
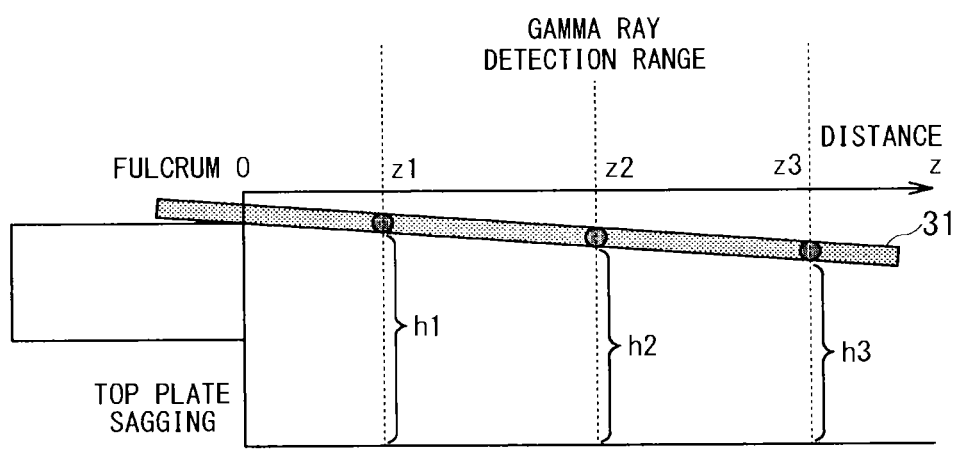
FIG. 4 illustrates an imaging range of a PET frame device according to the first embodiment, including bending of a top panel from a fulcrum of the top panel to a gamma ray detection range for detection of a gamma ray.

FIG. 4 illustrates an imaging range of the PET frame device 1 according to the first embodiment, including bending of the top panel 31 from the fulcrum 0 of the top panel 31 to a gamma ray detection range for detection of a gamma ray.

As shown in FIG. 4, the PET frame device 1 detects a gamma ray within an imaging range from a distance z1 to a distance z3 with a distance z2 at the center. In FIG. 4, with a regard to heights h of the top panel 31, a height h2 of the top panel 31 in an imaging position at the distance z2 is smaller than a height h1 of the top panel 31 in an imaging position at a distance z1, and a height h3 of the top panel 31 in an imaging position at a distance z3 is smaller than the heights of the top panel 31 in the imaging positions at the distances z1 and z2. The distances z1 to z3 indicate stroke amounts (protrusion amounts) of the top panel 31 from the fulcrum 0. The fulcrum 0 is an arbitrary reference position as a reference of the stroke amount.

As such, FIG. 4 shows that the top panel 31 bends downward in the sheet surface with increasing distance between the fulcrum 0 of the top panel 31 and the imaging position of the top panel 31. Bending of the top panel 31 (depression of the top panel 31) is sometimes referred to as top panel sagging, and an amount of bending of the top panel 31 is sometimes referred to as a top panel sagging amount.

Thus, the top panel sagging can be also expressed by the height h of the top panel 31.

Figure 5A:
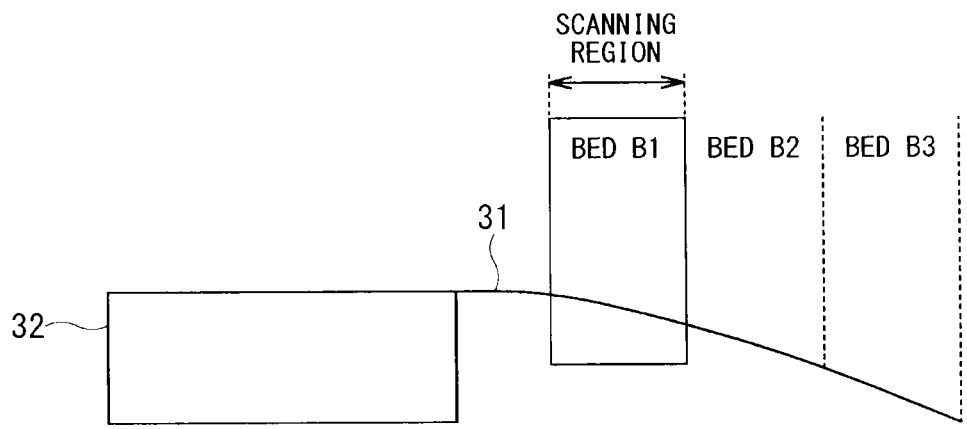
FIG. 5A to 5C illustrate top panel sagging in an image captured by a step-and-shoot method by the PET frame device according to the first embodiment.
Figure 5B:
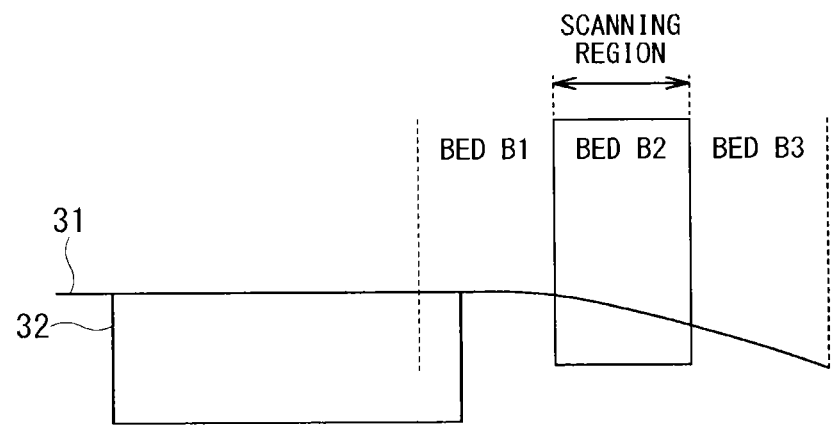
Figure 5C:
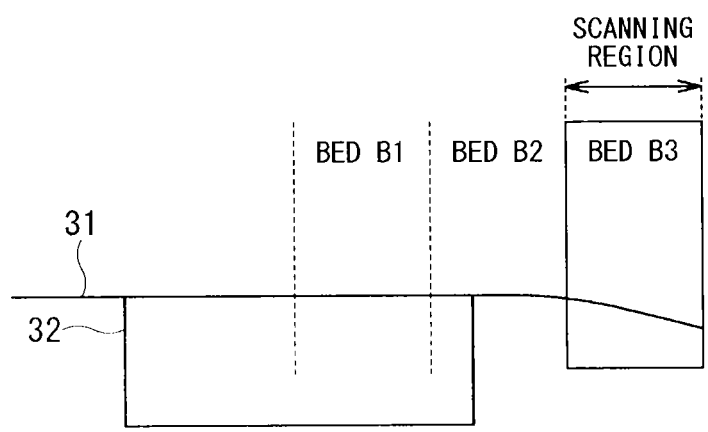

FIG. 5A to 5C illustrate top panel sagging in an imaging position in imaging by the step-and-shoot method by the PET frame device 1 according to the first embodiment. An imaging region of the PET image is described as a scanning region. A bed B1, a bed B2, and a bed B3 shown in FIG. 5A to 5C show imaging positions (imaging ranges) in the PET image. FIG. 5A to 5C shows top panel sagging when the subject P is placed on the top panel 31 although it does not show the subject P.

As shown in FIG. 5A to 5C, a top panel sagging amount differs depending on a stroke amount of the top panel 31 protruded from the bed 32. For example, as shown in FIG. 5A, when scanning is performed in the position of the bed B1 with the top panel 31 being protruded from the bed 32, a load by the subject P has a large impact on the top panel 31, which also increases a top panel sagging amount in the scanning region.

Meanwhile, as shown in FIGS. 5B and 5C, when the stroke amount of protrusion of the top panel 31 is reduced, the impact of the load by the subject P on the top panel 31 is reduced to also reduce the top panel sagging amount in the scanning region. Specifically, as shown in FIG. 5B, when scanning is performed in the position of the bed B2, the top panel sagging amount of the top panel 31 is smaller than the top panel sagging amount when scanning is performed in the position of the bed B 1. Also, as shown in FIG. 5C, when scanning is performed in the position of the bed B3, the top panel sagging amount of the top panel 31 is smaller than the top panel sagging amounts in the positions of the bed B1 and the bed B2.

Figure 6:
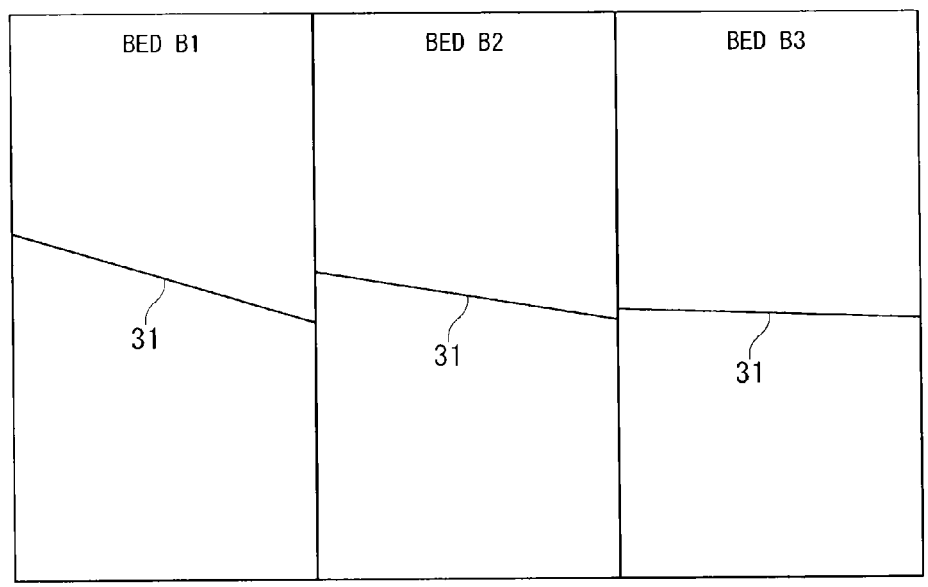
FIG. 6 illustrates a position of the top panel when the PET frame device according to the first embodiment images a subject by the step-and-shoot method.

FIG. 6 illustrates the imaging position of the top panel 31 when the PET frame device 1 according to the first embodiment images the subject P by the step-and-shoot method. The position of the top panel 31 indicates the height of the top panel 31 in the imaging position.

FIG. 6 shows a section of the subject P along the body axis when the PET frame device 1 images the top panel 31 in the positions of the bed B1, the bed B2, and the bed B3. Specifically, FIG. 6 shows that when the PET frame device 1 images the subject P by the step-and-shoot method, the top panel sagging amount differs depending on the imaging positions of the beds, and the positions of the top panel 31 differ among the beds. Next, the position of the top panel when the CT frame device 2 images the subject P by the helical scanning method will be described.

Figure 7:
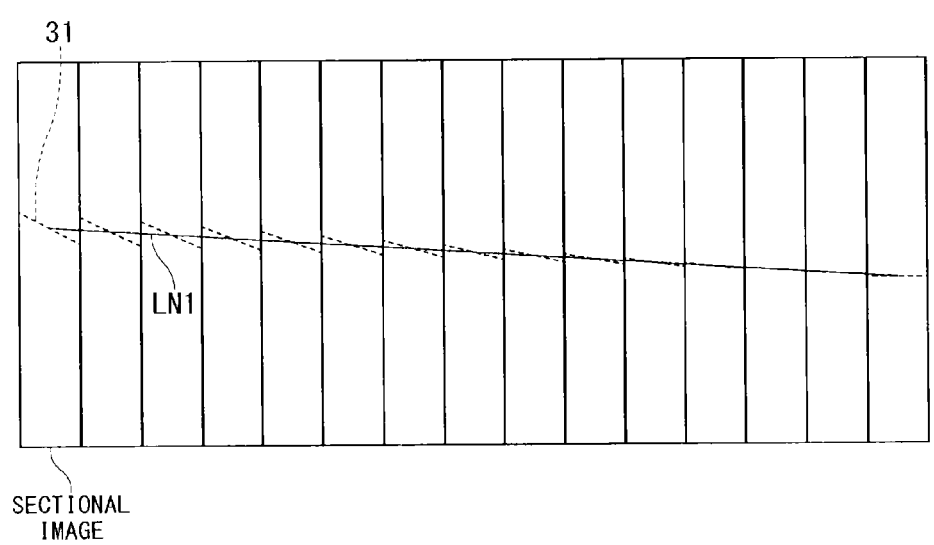
FIG. 7 illustrates a position of the top panel when a CT frame device according to the first embodiment images a subject by a helical scanning method.

FIG. 7 illustrates the position of the top panel 31 when the CT frame device 2 according to this embodiment images the subject P by the helical scanning method.

FIG. 7 shows a section of the top panel 31 along the body axis when the CT frame device 2 continuously images the top panel 31 by the helical scanning method. Specifically, when the CT frame device 2 images the top panel 31 by the helical scanning method, a plurality of captured sectional images are used to show the section of the top panel 31 along the body axis. A plurality of rectangles shown in FIG. 7 show a slice width of the sectional image. A line LN1 shown in FIG. 7 shows a line passing through the center of the top panel 31 in each sectional image.

When the CT frame device 2 images the subject P by the helical scanning method, the top panel sagging amount of the top panel 31 increases with increasing stroke amount of the top panel 31, and thus the height of the top panel 31 in each sectional image is gradually reduced with increasing stroke amount of the top panel 31.

The height of the top panel 31 when the X-ray CT image captured by the helical scanning method is viewed along the body axis is the line LN1 passing through the center of the top panel 31. Next, misalignment between the image captured by the step-and-shoot method and the image captured by the helical scanning method will be described.

Figure 8:
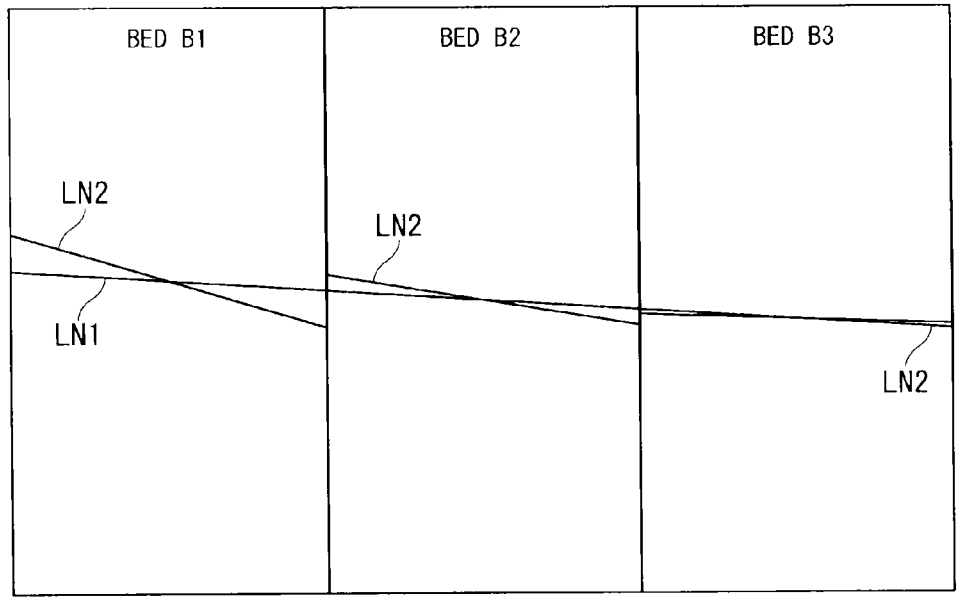
FIG. 8 illustrates misalignment between the image captured by the step-and-shoot method and the image captured by the helical scanning method.

FIG. 8 illustrates misalignment between the image captured by the step-and-shoot method and the image captured by the helical scanning method.

FIG. 8 shows a position (shown by a line LN2) of the top panel 31 in the image captured by the step-and-shoot method shown in FIG. 6, and a position (the line LN1 described above) of the top panel 31 in the image captured by the helical scanning method shown in FIG. 7.

As indicated by the line LN1 and the line LN2 in FIG. 8, the top panels 31 imaged by the imaging methods have different tilts, which causes misalignment between the captured images. Specifically, such misalignment between the top panels 31 causes misalignment between the PET image and the X-ray CT image in fusion of the images, thereby preventing correction with high accuracy and preventing a fusion image from being obtained.

Thus, in the PET-CT apparatus 100 according to the first embodiment, the correction unit 46 described above uses the top panel reference profile and the three-dimensional correction table to correct the PET image and the X-ray CT image to properly align the top panels 31, thereby allowing correction with high accuracy with fusion of the PET image and the X-ray CT image, and obtaining a fusion image.

The top panel reference profile refers to measurement data obtained by imaging a range that can be imaged by the helical scanning method without the subject P being placed on the top panel 31, and previously measuring the height of the top panel 31 or the top panel sagging amount without the subject P being placed thereon.

Figure 9:
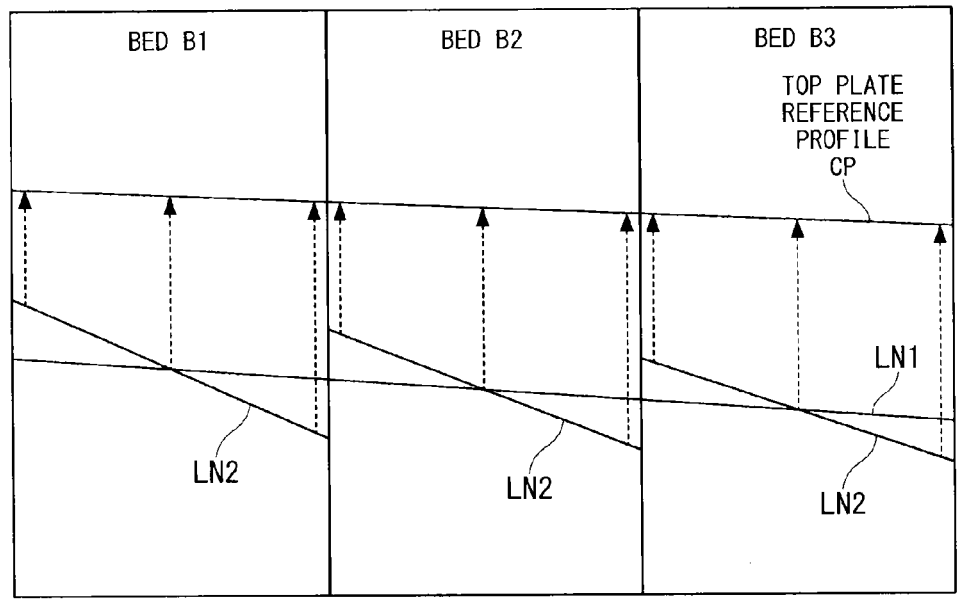
FIG. 9 illustrates a method for a correction unit according to the first embodiment to read a top panel reference profile and a three-dimensional correction table from a correction data storage unit, and correct a PET image and an X-ray CT image.

FIG. 9 illustrates a method for the correction unit 46 according to the first embodiment to read the top panel reference profile CP and the three-dimensional correction table from the correction data storage unit 45, and correct the PET image and the X-ray CT image.

FIG. 9 shows that the imaging position (line LN1) of the X-ray CT image captured by the helical scanning method is corrected to a position indicated by the top panel reference profile CP, estimates the tilt of the top panel 31 using the three-dimensional correction table in the imaging position (line LN2) of the PET image captured by the step-and-shoot method, and calculates a top panel position in each imaging position in imaging by the step-and-shoot method.

The correction unit 46 corrects the calculated top panel position to the top panel position indicated by the top panel reference profile CP. Thus, the correction unit 46 corrects the imaging position (line LN1) of the X-ray CT image to the top panel reference profile CP, and also corrects the imaging position (line LN2) of the PET image to the top panel reference profile CP. Thus, the correction unit 46 can fuse the corrected X-ray CT image and PET image in the position indicated by the top panel reference profile CP, thereby allowing correction with high accuracy and generation of a fusion image.

In the first embodiment, the position of the captured image is corrected to the position indicated by the top panel reference profile CP, and thus corrected to match the height of the top panel 31 with the subject P being not placed on the top panel 31. Specifically, the correction unit 46 corrects the top panel sagging amount caused by the subject P being placed on the top panel 31 to the height of the top panel 31 with the subject P being not placed on the top panel 31.

Next, the three-dimensional correction table stored in the correction data storage unit 45 according to the first embodiment will be described.

Figure 10:
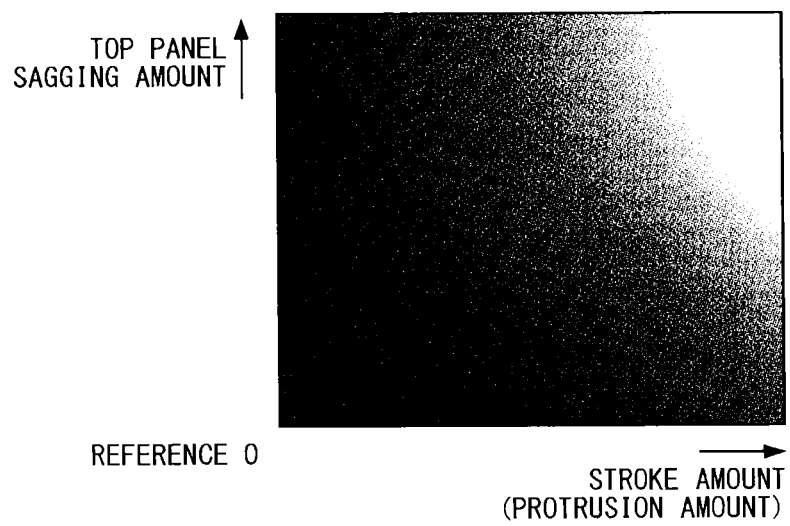
FIG. 10 illustrates a three-dimensional correction table for estimating a tilt of the top panel, stored in the correction data storage unit according to the first embodiment.

FIG. 10 illustrates the three-dimensional correction table for estimating the tilt of the top panel 31, stored in the correction data storage unit 45 according to the first embodiment.

As shown in FIG. 10, the correction table estimates the tilt of the top panel 31 in imaging by the step-and-shoot method based on a stroke amount (protrusion amount) of the top panel 31 in the imaging position in imaging by the helical scanning method and a top panel sagging amount (top panel bending amount). In the correction table, the tilt of the top panel 31 in the imaging position in imaging by the step-and-shoot method is associated based on the stroke amount of the top panel 31 protruded from the bed 32, and the top panel sagging amount in the imaging position corresponding to the stroke amount.

In the first embodiment, the three-dimensional correction table (first correction table) can be used to align the tilts of the top panel 31 in the imaging position in imaging by the helical scanning method and the imaging position in imaging by the step-and-shoot method.

In FIG. 10, a right upper part of the correction table is pale white, and the tilt of the top panel 31 increases with increasing whiteness of this part, while the tilt of the top panel 31 decreases with increasing blackness of this part. The three-dimensional correction table is previously compiled into a database and stored in the correction data storage unit 45.

Next, the correction unit 46 in the console device 4 of the PET-CT apparatus 100 will be described.

Figure 11:
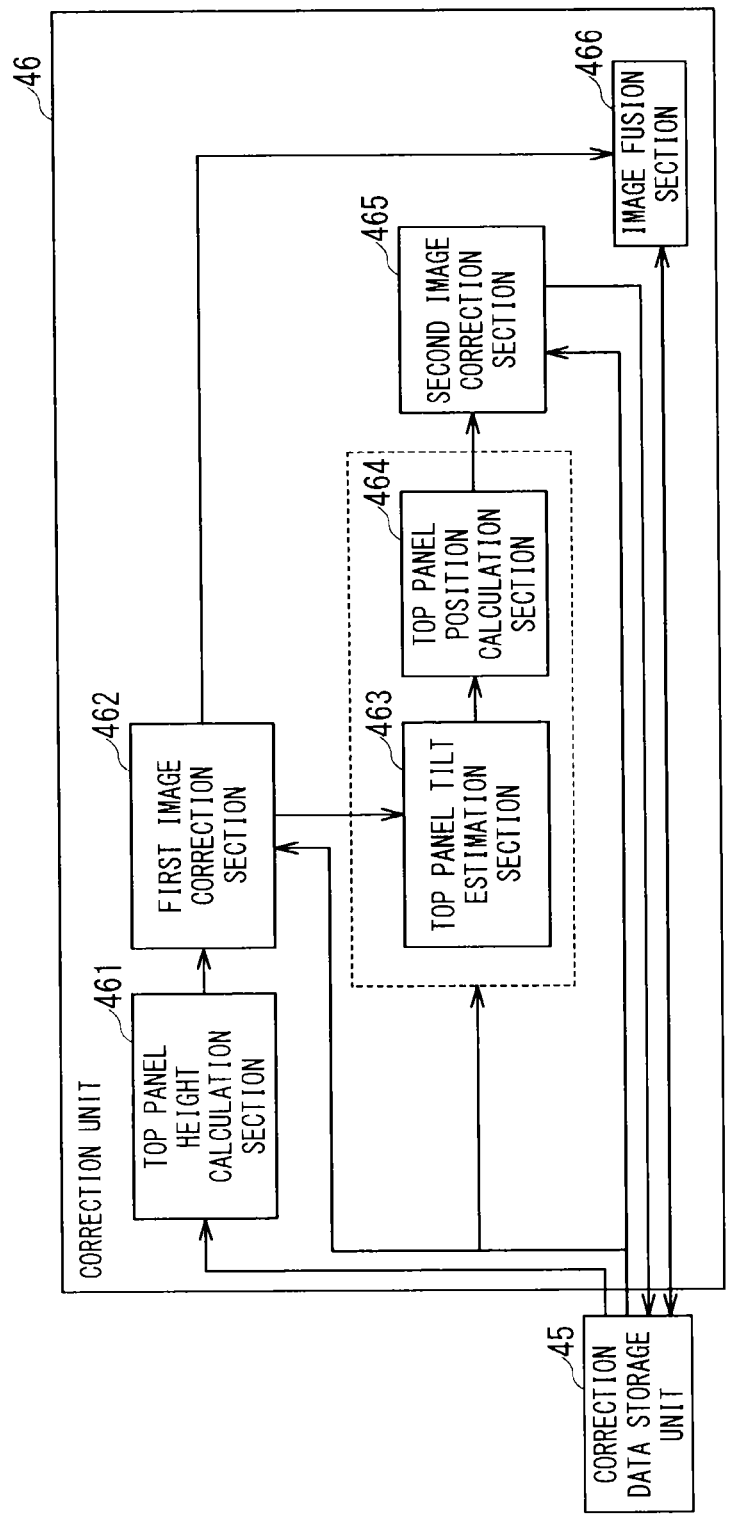
FIG. 11 is a functional block diagram showing a configuration of a correction unit in the console device of the PET-CT apparatus according to the first embodiment.

FIG. 11 is a functional block diagram showing a configuration of the correction unit 46 in the console device 4 of the PET-CT apparatus 100 according to the first embodiment.

As shown in FIG. 11, the correction unit 46 includes a top panel height calculation section 461, a first image correction section (first captured image correction section) 462, a top panel tilt estimation section 463, a top panel position calculation section 464, a second image correction section (second captured image correction section) 465, and an image fusion section 466. The top panel tilt estimation section 463 and the top panel position calculation section 464 constitute an imaging position estimation unit, and the second image correction section 465 constitutes an image correction unit.

The correction unit 46 is connected to the correction data storage unit 45. Thus, the correction unit 46 can read the X-ray CT image and the PET image stored in the correction data storage unit 45.

The top panel height calculation section 461 calculates a height h of the top panel 31 corresponding to a distance between the fulcrum 0 of the top panel 31 and the imaging position, from the image captured by continuous imaging of the subject P by the helical scanning method.

The first image correction section 462 corrects a difference between the height of the top panel 31 calculated by the top panel height calculation section 461, and the height of the top panel defined by the top panel reference profile CP stored in the correction data storage unit 45. Specifically, the first image correction section 462 corrects the height of the top panel 31 in the imaging position to the height of the top panel 31 in the imaging position with the subject P being not placed on the top panel 31.

The top panel tilt estimation section 463 considers the difference in the height of the top panel 31 as a bending amount of the top panel 31 based on the stroke amount of the top panel 31 in the imaging position in continuous imaging of the subject P by the helical scanning method, the difference in the height of the top panel 31 corrected by the first image correction section 462, and the three-dimensional correction table, and estimates the tilt of the top panel 31 in the imaging position in imaging of the subject P by the step-and-shoot method as an example of a different imaging method.

The top panel position calculation section 464 calculates the top panel position (the height h of the top panel 31 and the tilt of the top panel 31) in the imaging position in imaging by the step-and-shoot method, from the tilt of the top panel 31 estimated by the top panel tilt estimation section 463 in the imaging position in imaging by the step-and-shoot method.

The second image correction section 465 corrects the top panel position (the height h of the top panel 31 and the tilt of the top panel 31) calculated by the top panel position calculation section 464 to the top panel position defined by the top panel reference profile CP like the first image correction section 462. Specifically, the second image correction section 465 calculates a correction amount for correcting the height h of the top panel 31 and the tilt of the top panel 31 in the imaging position calculated by the top panel position calculation section 464 to the height of the top panel 31 and the tilt of the top panel 31 in the imaging position with the subject P being not placed on the top panel 31.

The correction amount for correcting the calculated top panel position to the height of the top panel 31 and the tilt of the top panel 31 defined by the top panel reference profile CP is also referred to as a top panel sagging correction amount. The second image correction section 465 stores the calculated top panel sagging correction amount in the correction data storage unit 45.

The top panel reference profile CP is linear data indicating the height (position) of the top panel, and the top panel position calculated by the top panel position calculation section 464 is data on the height h of the top panel 31 and the tilt of the top panel in the imaging position. Thus, the top panel position including the height h of the top panel 31 and the tilt of the top panel in the imaging position can be applied to the image (for example, the PET image) captured by the step-and-shoot method to allow alignment of the captured image with the height (position) indicated by the top panel reference profile CP.

Next, the attenuation map generation unit 50 (FIG. 3) reads the top panel sagging correction amount from the correction data storage unit 45, and corrects the attenuation map to the position of the PET image based on the top panel sagging correction amount.

In this case, the PET reconfiguration unit 44 (FIG. 3) performs attenuation correction of the PET image using the corrected attenuation map.

The image fusion section 466 (FIG. 11) reads the PET image having subjected to the attenuation correction and the top panel sagging correction amount from the correction data storage unit 45, and corrects the PET image having subjected to the attenuation correction to the top panel position by the top panel reference profile CP. Then, the image fusion section 466 fuses the X-ray CT image (first captured image) corrected by the first image correction section 462 and the corrected PET image. The image fusion section 466 stores the fusion image in the correction data storage unit 45.

Thus, the control unit 47 (FIG. 3) can read the fusion image from the correction data storage unit 45 based on an instruction of an operator who operates the PET-CT apparatus 100, input from an input unit (not shown), and display the fusion image on the display unit (not shown).

As described above, in the PET-CT apparatus 100 according to this embodiment, the correction unit 46 in the console device 4 corrects the imaging position of the X-ray CT image captured by the helical scanning method to the position indicated by the top panel reference profile CP, estimates the tilt of the top panel 31 in the imaging position of the PET image captured by the step-and-shoot method, and corrects the estimated height h of the top panel 31 and tilt of the top panel 31 to the position indicated by the top panel reference profile CP.

As such, in the PET-CT apparatus 100, the PET frame device 1 images the subject P by the step-and-shoot method, and even if the top panel 31 is not projected on the PET image, the X-ray CT image captured by the helical scanning method by the CT frame device 2, the top panel reference profile CP, and the three-dimensional correction table for estimating the tilt of the top panel 31 in imaging by the step-and-shoot method can be used to correct the X-ray CT image and the PET image.

Thus, the PET-CT apparatus 100 according to this embodiment can superimpose and fuse the corrected PET image and X-ray CT image to perform correction with high accuracy and generate a fusion image.

Next, a general procedure of an imaging process of the PET-CT apparatus 100 according to this embodiment will be described.

Figure 12:
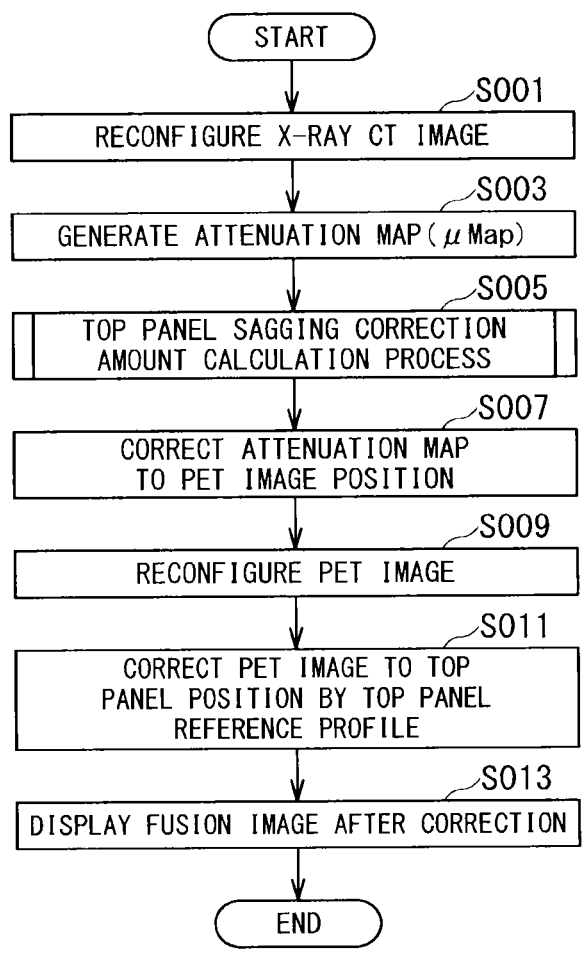
FIG. 12 is a flowchart showing a general procedure of an imaging process of the PET-CT apparatus according to the first embodiment.

FIG. 12 is a flowchart showing a general procedure of an imaging process of the PET-CT apparatus 100 according to the first embodiment. FIG. 12 shows a general operation after an X-ray CT examination by the helical scanning method and a PET examination by the step-and-shoot method for the subject P have been conducted.

First, in the PET-CT apparatus 100 according to this embodiment, the CT image reconfiguration unit 42 (FIG. 3) provided in the console device 4 uses the X-ray projection data stored in the X-ray projection data storage unit 41 to reconfigure the X-ray CT image (step S001). Then, the CT image reconfiguration unit 42 stores the reconfigured X-ray CT image in the correction data storage unit 45 and delivers the X-ray CT image to the attenuation map generation unit 50.

Then, the attenuation map generation unit 50 (FIG. 3) uses the X-ray CT image reconfigured by the CT image reconfiguration unit 42 to generate an attenuation map (μMap) for correcting attenuation of a gamma ray (step S003).

Then, the correction unit 46 reads the reconfigured X-ray CT image and the three-dimensional correction table from the correction data storage unit 45 to perform a top panel sagging correction amount calculation process (first correction amount calculation process) for calculating a top panel sagging correction amount (step S005). The correction unit 46 stores the calculated top panel sagging correction amount in the correction data storage unit 45.

Then, the attenuation map generation unit 50 reads the top panel sagging correction amount from the correction data storage unit 45, corrects the attenuation map to a PET image position (step S007), and stores the corrected attenuation map in the correction data storage unit 45.

Then, the PET reconfiguration unit 44 (FIG. 3) uses gamma ray projection data stored in the gamma ray projection data storage unit 43 to reconfigure the PET image (step S009). In this case, the PET reconfiguration unit 44 reads the attenuation map from the correction data storage unit 45, and uses the gamma ray projection data and the read attenuation map to reconfigure the PET image (attenuation correction).

Then, the PET reconfiguration unit 44 stores the reconfigured PET image in the correction data storage unit 45.

Next, the image fusion section 466 (FIG. 11) in the correction unit 46 reads the PET image having subjected to attenuation correction by the PET reconfiguration unit 44 and the top panel sagging correction amount from the correction data storage unit 45, and corrects the PET image having subjected to attenuation correction to the top panel position by the top panel reference profile CP (step S011).

Then, the image fusion section 466 in the correction unit 46 fuses the X-ray CT image and the PET image corrected to the top panel position by the top panel reference profile CP to generate a fusion image, and stores the generated fusion image in the correction data storage unit 45. The control unit 47 reads the fusion image stored in the correction data storage unit 45, and displays the fusion image on a display unit (not shown) in the console device 4 (step S013).

As such, in the PET-CT apparatus 100 according to this embodiment, the correction unit 46 calculates the top panel sagging correction amount for correcting the PET image and generates the fusion image, the control unit 47 displays the fusion image on the display unit, and the process is finished. Next, the top panel sagging amount calculation process for the correction unit 46 to calculate the top panel sagging correction amount will be described.

Figure 13:
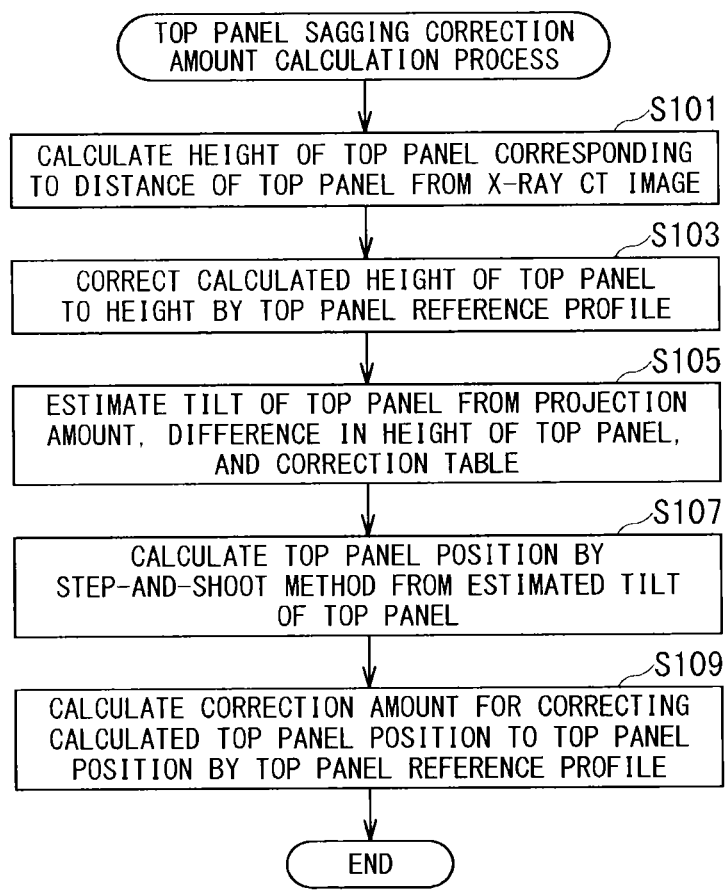
FIG. 13 is a flowchart showing a procedure of a top panel sagging correction amount calculation process for calculating a top panel sagging correction amount in the correction unit (FIG. 11) of the PET-CT apparatus according to the first embodiment.

FIG. 13 is a flowchart showing a procedure of the top panel sagging correction amount calculation process (first correction amount calculation process) for calculating a top panel sagging correction amount in the correction unit 46 (FIG. 11) of the PET-CT apparatus 100 according to the first embodiment.

As shown in FIG. 13, the top panel height calculation section 461 (FIG. 11) in the correction unit 46 calculates the height h of the top panel 31 corresponding to the distance between the fulcrum 0 of the top panel 31 and the imaging position from the image captured by continuous imaging of the subject P by the helical scanning method (step S101).

Then, the first image correction section 462 (FIG. 11) corrects a difference between the height h of the top panel 31 calculated from the image captured by the helical scanning method, and the height of the top panel defined by the top panel reference profile CP stored in the correction data storage unit 45. Specifically, the first image correction section 462 corrects the calculated height h of the top panel 31 to the height of the top panel 31 in the imaging position with the subject P being not placed on the top panel 31 (step S103).

Then, the top panel tilt estimation section 463 (FIG. 11) considers the difference in the height of the top panel 31 as a bending amount of the top panel 31 based on the stroke amount of the top panel 31 in the imaging position in continuous imaging by the helical scanning method, the difference in the height of the top panel 31 corrected by the first image correction section 462, and the three-dimensional correction table, and estimates the tilt of the top panel in the imaging position in imaging by the step-and-shoot method as a different imaging method (step S105).

Specifically, the difference in the height of the top panel 31 is considered as a bending amount of the top panel 31 based on the stroke amount of the top panel 31 in the distance between the fulcrum 0 of the top panel 31 and the imaging position calculated in step S101, the difference in the height of the top panel corrected in step S103, and the three-dimensional correction table shown in FIG. 10 to estimate the tilt of the top panel in the imaging position in imaging by the step-and-shoot method.

Next, the top panel position calculation section 464 (FIG. 11) calculates a top panel position (the height h of the top panel 31 and the tilt of the top panel 31) in the imaging position in imaging by the step-and-shoot method, from the tilt of the top panel 31 estimated by the top panel tilt estimation section 463 in the imaging position in imaging by the step-and-shoot method (step S107).

Then, the second image correction section 465 (FIG. 11) corrects the top panel position (the height h of the top panel 31 and the tilt of the top panel 31) calculated by the top panel position calculation section 464 to the top panel position defined by the top panel reference profile CP like the first image correction section 462. Specifically, the second image correction section 465 calculates a top panel sagging correction amount for correcting the height h of the top panel 31 and the tilt of the top panel 31 in the imaging position calculated by the top panel position calculation section 464 to the height of the top panel 31 and the tilt of the top panel 31 in the imaging position with the subject P being not placed on the top panel 31 (step S109).

As described above, in the PET-CT apparatus 100 according to this embodiment, the correction unit 46 corrects the imaging position of the X-ray CT image captured by the helical scanning method to the position indicated by the top panel reference profile CP, estimates the tilt of the top panel in the imaging position of the PET image captured by the step-and-shoot method, and corrects the estimated tilt of the top panel and the imaging position in imaging by the step-and-shoot method to the position indicated by the top panel reference profile CP.

Thus, in the PET-CT apparatus 100 according to this embodiment, the PET frame device 1 images the subject P by the step-and-shoot method, and even if the top panel 31 is not projected on the PET image, the X-ray CT image captured by the helical scanning method by the CT frame device 2, the top panel reference profile CP, and the three-dimensional correction table for estimating the tilt of the top panel in imaging by the step-and-shoot method can be used to correct the X-ray CT image and the PET image.

Thus, the PET-CT apparatus 100 according to this embodiment can superimpose and fuse the corrected PET image and X-ray CT image to perform correction with high accuracy and generate a fusion image.

The PET-CT apparatus 100 uses the PET frame device 1 to generate the PET image, but in the first embodiment, for example, a single photon emission computed tomography apparatus (SPECT apparatus) may be used.

In the above described first embodiment, the PET-CT apparatus 100 including the CT frame device 2 that images the subject P by the helical scanning method, and the PET frame device 1 that images the subject P by the step-and-shoot method has been described, but the first embodiment is not limited to this.

Specifically, modality may be used in which the subject P is imaged by the helical scanning method as a first imaging method, and the subject P is imaged by the step-and-shoot method as a second imaging method. For example, after the CT frame device 2 images the subject P by the helical scanning method, the CT frame device different from the CT frame device 2 may be used to image the subject P by the step-and-shoot method.

When the CT frame device images the subject P by the step-and-shoot method, the top panel position of the top panel 31 of the bed device 3 is imaged, and thus the tilt of the top panel of the top panel 31 to be imaged and the imaging position of the top panel 31 may be corrected to the position defined by the top panel reference profile CP.

Second Embodiment

In the first embodiment, as an example of a correction table, the three-dimensional correction table (first correction table) for estimating the tilt of the top panel 31 based on the stroke amount from the fulcrum of the top panel 31 to the imaging position, and the bending amount of the top panel 31 corresponding to the stroke amount is used to correct the top panel sagging amount.

In the second embodiment, as another example of the correction table, a three-dimensional correction table (second correction table) in which a distance between a fulcrum of a top panel 31 and an imaging position of a subject P, a load of the subject P, and a height of the top panel 31 in an imaging position are associated is used to estimate the load of the subject P and the height h of the top panel 31.

A schematic configuration of a PET-CT apparatus according to the second embodiment is the same as that shown in FIGS. 1 to 8, and descriptions thereof will be omitted.

Figure 14:
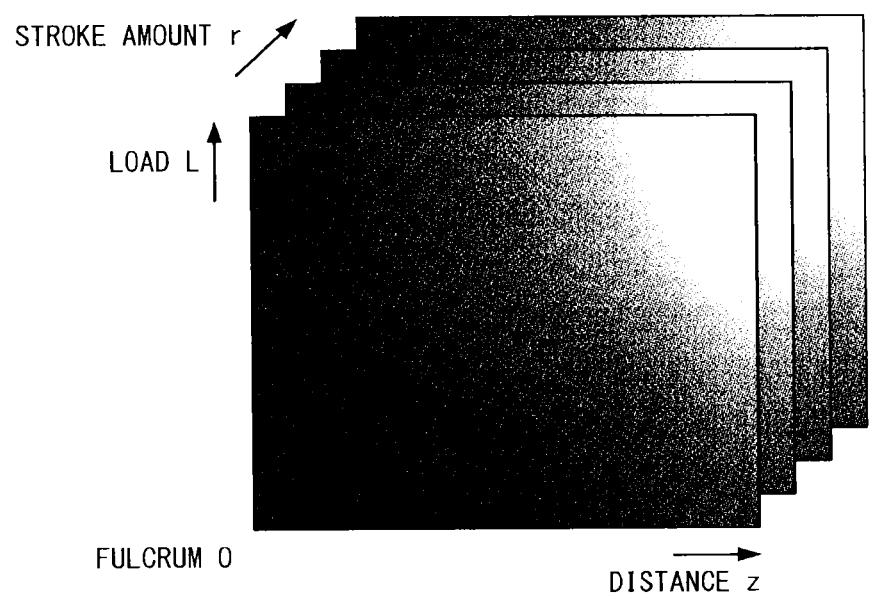
FIG. 14 illustrates a three-dimensional correction table for estimating a height of a top panel, stored in a correction data storage unit according to a second embodiment.

FIG. 14 illustrates a three-dimensional correction table for estimating the height h of the top panel 31 stored in a correction data storage unit according to the second embodiment.

As shown in FIG. 14, the correction table estimates the height h of the top panel 31 based on three parameters: a distance z between the fulcrum 0 of the top panel 31 and the imaging position, a load L in the imaging position, and a stroke amount r of the top panel 31 protruded from a bed 32. In the correction table, previously measured values of the top panel 31 are tabulated. Specifically, the height h of the top panel 31 when a subject P to be measured is placed is measured for a plurality of subjects P, and the height h of the top panel 31 is expressed with the three parameters in the correction table.

In FIG. 14, a right upper part of the correction table is pale white, and the height h of the top panel decreases with increasing whiteness of this part, while the height h of the top panel increases with increasing blackness of this part. As such, in the second embodiment, the height h of the top panel can be estimated based on the correction table, and thus a top panel sagging correction amount for correcting the height h of the top panel can be estimated.

Details of the correction table will be described two-dimensionally.

Figure 15A:
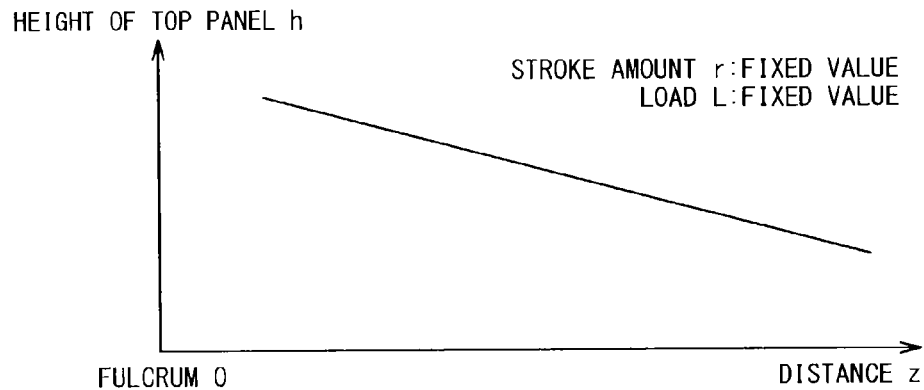
FIG. 15A to 15C illustrate the three-dimensional correction table according to the second embodiment expressed two-dimensionally.
Figure 15B:
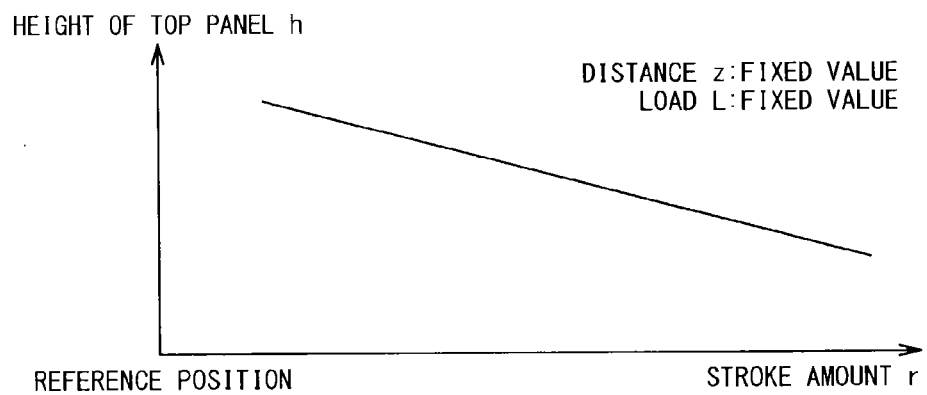
Figure 15C:
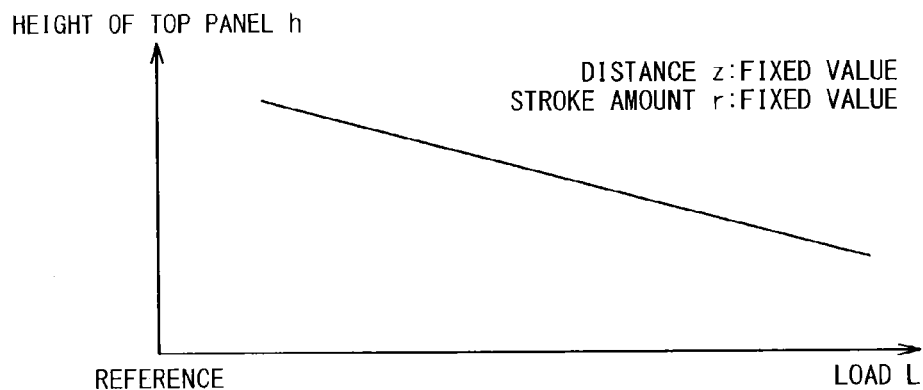

FIG. 15A to 15C illustrate the three-dimensional correction table according to the second embodiment expressed two-dimensionally.

FIG. 15A shows a distance z from the fulcrum 0 of the top panel 31 (see FIG. 4) as a reference position on the abscissa, and the height h of the top panel 31 corresponding to the distance z on the ordinate by coordinate conversion. FIG. 15A shows that the height h of the top panel 31 decreases with increasing distance z from the fulcrum 0 of the top panel 31. In FIG. 15A, a stroke amount r of the top panel 31, and the load L in the imaging position are fixed values.

FIG. 15B shows a stroke amount r from a reference position that is a position before protrusion of the top panel 31 on the abscissa, and the height h of the top panel 31 corresponding to the stroke amount r on the ordinate by coordinate conversion. FIG. 15B shows that the height h of the top panel decreases with increasing stroke amount r from the reference position. In FIG. 15B, the distance z between the fulcrum 0 of the top panel 31 and the imaging position, and the load L in the imaging position are fixed values.

FIG. 15C shows a load L from a reference state where no load L is applied in the imaging position of the top panel 31 on the abscissa, and the height h of the top panel 31 corresponding to the load L on the ordinate by coordinate conversion. FIG. 15C shows that the height h of the top panel decreases with increasing load L in the imaging position. In FIG. 15C, the distance z between the fulcrum 0 of the top panel 31 and the imaging position and the stroke amount r of the top panel 31 are fixed values.

As such, the three-dimensional correction table shown in FIG. 14 can estimate the height h of the top panel 31 based on the three parameters: the distance z between the fulcrum 0 of the top panel 31 and the imaging position, the load L in the imaging position, and the stroke amount r of the top panel 31 protruded from the bed 32 shown in FIGS. 15A, 15B, and 15C.

Figure 16:
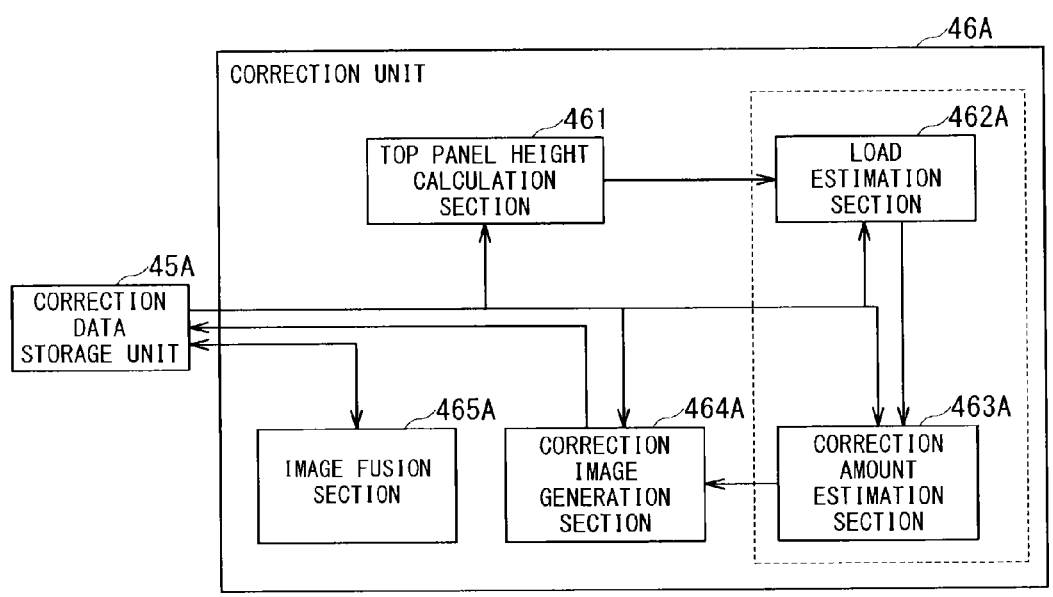
FIG. 16 is a functional block diagram showing a configuration of a correction unit of a PET-CT apparatus according to the second embodiment.

FIG. 16 is a functional block diagram showing a configuration of a correction unit 46A of the PET-CT apparatus according to the second embodiment. The same components are denoted by the same reference numerals, and descriptions thereof will be omitted.

As shown in FIG. 16, the correction unit 46A includes a top panel height calculation section 461, a load estimation section 462A, a correction amount estimation section 463A, a correction image generation section 464A, and an image fusion section 465A. The load estimation section 462A and the correction amount estimation section 463A constitute an imaging position estimation unit. The correction image generation section 464A constitutes an image correction unit. The correction unit 46A is connected to a correction data storage unit 45A. Thus, the correction unit 46A can read the X-ray CT image or the PET image stored in the correction data storage unit 45A.

As in the first embodiment, the top panel height calculation section 461 calculates the height h of the top panel 31 corresponding to the distance between the fulcrum 0 of the top panel 31 and the imaging position, from the image captured by the helical scanning method.

The load estimation section 462A estimates a load L of the subject P applied to the top panel 31 based on the calculated height h of the top panel 31, the distance z between the fulcrum 0 of the top panel 31 and the imaging position of the subject P, and the correction table stored in the correction data storage unit 45A (FIG. 14). In this case, since the load L of the subject P applied to the top panel 31 is constant (fixed value), the same value is obtained both by the helical scanning method and the step-and-shoot method. Thus, the load estimation section 462A reads a three-dimensional correction table from the correction data storage unit 45A, estimates the load L when the CT frame device 2 images the subject P by the helical scanning method, and estimates the load L as a load L in imaging of the subject P by the step-and-shoot method by the PET frame device 1.

The correction amount estimation section 463A estimates the height h of the top panel 31 in an imaging range in imaging of the subject P by the step-and-shoot method based on the distance z between the fulcrum 0 of the top panel 31 and the imaging position in imaging of the subject P by the step-and-shoot method, the load L of the subject P estimated by the load estimation section 462A, and the three-dimensional correction table.

Specifically, the correction amount estimation section 463A calculates an imaging range in imaging of the subject P by the step-and-shoot method from a distance z2 (see FIG. 4), reads the three-dimensional correction table (see FIG. 14) stored in the correction data storage unit 45A, and estimates the height h of the top panel 31 in the imaging range from the load L of the subject P in the imaging range. A method of estimating the height h of the top panel 31 in the imaging range will be described with reference to the drawings.

Figure 17:
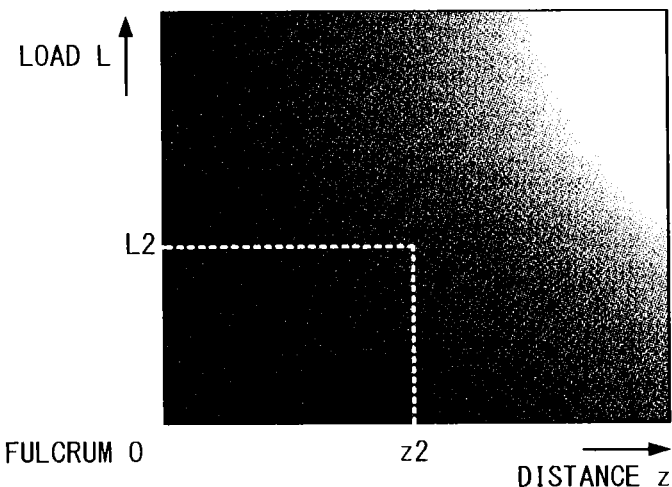
FIG. 17 illustrates an example of the three-dimensional correction table in which a load calculation unit (FIG. 16) according to the second embodiment reads the three-dimensional correction table from the correction data storage unit, and estimates a load in a central position of an imaging range in imaging by a step-and-shoot method.

FIG. 17 illustrates an example of the three-dimensional correction table in which the load calculation section 462A (FIG. 16) according to the second embodiment reads the three-dimensional correction table from the correction data storage unit 45A, and estimates the load L in a central position of the imaging range in imaging by the step-and-shoot method.

First, a center of the imaging range for imaging the subject P from the fulcrum 0 of the top panel 31 by the step-and-shoot method is the distance z2 (see FIG. 4). The load calculation section 462A reads the three-dimensional correction table (FIG. 17) stored in the correction data storage unit 45A, and estimates a load L2 on the top panel 31 from the height h of the top panel 31 at the distance z2 in the image captured by the helical scanning method, and the distance z2. The load L2 in the distance z2 is the same within the imaging range (from z1 to z3).

Next, the correction amount estimation section 463A refers to the three-dimensional correction table, and calculates the heights h of the top panel 31 at the distance z1 and the distance z3.

Figure 18:
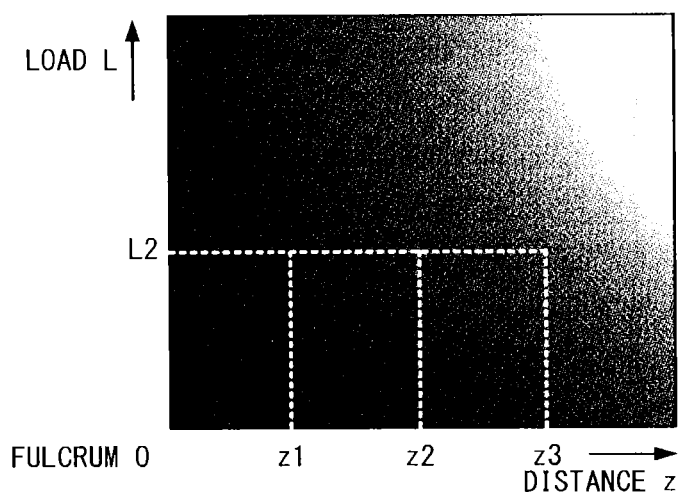
FIG. 18 illustrates an example in which a correction amount estimation unit according to the second embodiment refers to the three-dimensional correction table and estimates a height of the top panel under a load at each distance from a fulcrum of the top panel.

FIG. 18 illustrates an example where the correction amount estimation section 463A according to the second embodiment refers to the three-dimensional correction table, and estimates the height h of the top panel 31 under the load L2 at each distance from the fulcrum 0 of the top panel 31.

As shown in FIG. 18, the correction amount estimation section 463A (FIG. 16) refers to the three-dimensional correction table, and estimates the height h of the top panel 31 at the distance z1 and the distance z3 in the imaging range. In this case, the correction amount estimation section 463A refers to the three-dimensional correction table to calculate the load L2 at the distance z2 and a point of intersection of the distance z1 and the distance z3 to estimate each height h of the top panel 31 at the point.

Thus, the correction amount estimation section 463A can estimate the height h of the top panel 31 at each distance, and thus can estimate the height (or the top panel sagging amount) of the top panel to be corrected.

In FIG. 18, the height h of the top panel 31 is expressed by contrast. The contrast in FIG. 18 shows that the height h of the top panel 31 decreases and the top panel sagging amount increases with increasing whiteness of a white part, while the height h of the top panel 31 increases and the top panel sagging amount decreases with increasing blackness of a black part.

With reference to FIG. 4, an estimation process for estimating the height h of the top panel 31 will be described.

As shown in FIG. 4, at the distance z2 at the center of the imaging range, the load calculation section 462A (FIG. 16) estimates the load L2 on the top panel 31. The correction amount estimation section 463A refers to the three-dimensional correction table, and estimates a height h1 of the top panel 31 at the distance z1 and a height h3 of the top panel 31 at the distance z3.

The correction image generation section 464A calculates a correction amount (top panel sagging correction amount) for correction to the height h of the top panel 31 imaged by the step-and-shoot method based on the height h of the top panel 31 estimated by the correction amount estimation section 463A. The correction image generation section 464A stores the calculated top panel sagging correction amount in the correction data storage unit 45A.

The correction image generation section 464A has a function of correcting the PET image stored in the correction data storage unit 45. Specifically, the correction image generation section 464A can correct the height of the PET image captured by the step-and-shoot method based on the height h of the top panel 31 estimated by the correction amount estimation section 463A to generate a captured image (PET image). Then, the correction image generation section 464A stores the corrected PET image in the correction data storage unit 45A.

The image fusion section 465A reads the corrected PET image from the correction data storage unit 45A, and reads the X-ray CT image captured by the helical scanning method from the correction data storage unit 45A. The image fusion section 465A fuses the read PET image and X-ray CT image, and stores the fusion image in the correction data storage unit 45A.

Thus, the control unit reads the fusion image from the correction data storage unit 45A based on an instruction of an operator who operates the PET-CT apparatus, input from an input unit (not shown), and displays the fusion image on the display unit (not shown).

As such, in the PET-CT apparatus according to the second embodiment, the correction unit 46A refers to the three-dimensional correction table from the height h of the top panel 31 in the X-ray CT image to estimate the load L on the top panel 31 in the X-ray CT image captured by the helical scanning method. The load L is of the same value as the load L on the top panel 31 in the PET image captured by the step-and-shoot method. Thus, the correction unit 46A can estimate the height h of the top panel 31 in the imaging range of the PET image from the load L on the top panel 31 and the distance z to the imaging position to correct the position of the PET image in the imaging range.

Thus, in the PET-CT apparatus according to the second embodiment, the PET frame device 1 images the subject P by the step-and-shoot method, and even if the top panel 31 is not projected on the PET image, the height of the top panel 31 in the X-ray CT image captured by the helical scanning method by the CT frame device 2 and the three-dimensional correction table can be used to estimate the height h of the top panel 31 in the PET image and correct the position of the PET image.

Thus, the PET-CT apparatus according to the second embodiment can superimpose and fuse the corrected PET image and X-ray CT image to perform correction with high accuracy and generate a fusion image.

Next, a general procedure of an imaging process of the PET-CT apparatus according to the second embodiment will be described.

Figure 19:
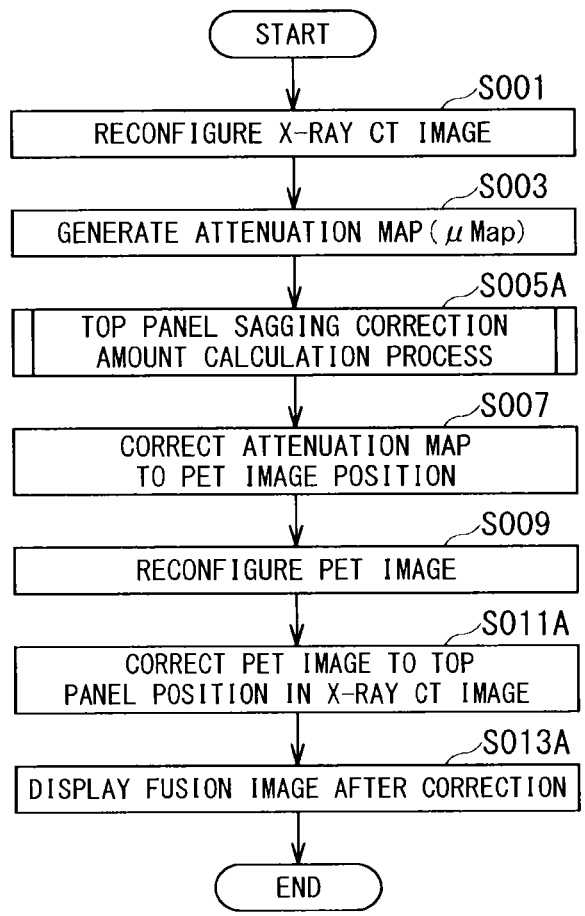
FIG. 19 is a flowchart showing a general procedure of an imaging process of the PET-CT apparatus according to the second embodiment.

FIG. 19 is a flowchart showing a general procedure of an imaging process of the PET-CT apparatus according to the second embodiment. FIG. 19 shows a general operation after an X-ray CT examination by the helical scanning method and a PET examination by the step-and-shoot method for the subject have been conducted. The same processes as in FIG. 12 are denoted by the same reference numerals, and descriptions thereof will be omitted.

The flowchart in FIG. 19 is different from the flowchart in FIG. 12 in a top panel sagging correction amount calculation process (second correction amount calculation process) in step S005A, and a process for correcting a PET image to a top panel position in an X-ray CT image in step S011A.

The correction unit 46A reads a reconfigured X-ray CT image and a three-dimensional correction table from the correction data storage unit 45A (FIG. 16), and calculates a top panel sagging correction amount by the top panel sagging correction amount calculation process (second correction amount calculation process) different from that in the first embodiment (step S005A). The correction unit 46A stores the calculated top panel sagging correction amount in the correction data storage unit 45A.

In step S007 and step S009, the top panel sagging correction amount calculated in step S005A is used to perform the same processes as in the first embodiment.

An image fusion section 465A (FIG. 16) in the correction unit 46A reads a PET image having subjected to attenuation correction by the PET reconfiguration unit 44 (FIG. 3) and a top panel sagging correction amount from the correction data storage unit 45A, and corrects the PET image having subjected to attenuation correction to the top panel position in the X-ray CT image (step S011A).

Thus, the image fusion section 465A in the correction unit 46A fuses the X-ray CT image and the PET image corrected to the top panel position in the X-ray CT image to generate a fusion image, and stores the generated fusion image in the correction data storage unit 45. The control unit 47 reads the fusion image stored in the correction data storage unit 45, and displays the fusion image on the display unit (not shown) in the console device 4 (step S013A).

As such, in the PET-CT apparatus according to the second embodiment, the correction unit 46A corrects the position of the PET image, generates the fusion image, displays the fusion image on the display unit, and thus finishes the process. Next, detailed operations of the correction unit 46A will be described.

Figure 20:
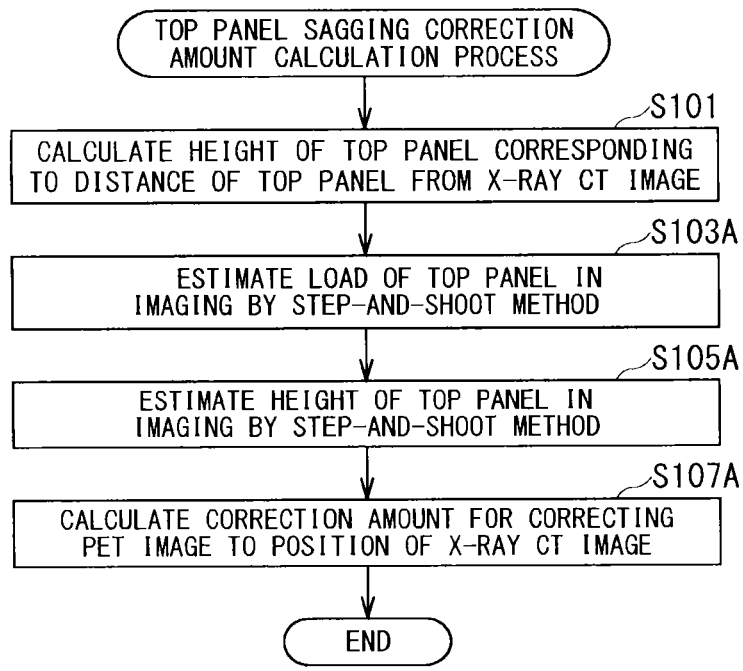
FIG. 20 is a flowchart showing a procedure of a PET image position correction process for correcting a position (height) of a PET image in the correction unit (FIG. 16) of the PET-CT apparatus according to the second embodiment.

FIG. 20 is a flowchart showing a procedure of the top panel sagging correction amount calculation process (second correction amount calculation process) for correcting a position (height) of the PET image in the correction unit 46A (FIG. 16) of the PET-CT apparatus according to the second embodiment. The same processes are denoted by the same reference numerals, and descriptions thereof will be omitted.

As shown in FIG. 20, in the correction unit 46A, as in the first embodiment, the top panel height calculation section 461 reads an X-ray CT image captured by the helical scanning method from the correction data storage unit 45A, and calculates the height h of the top panel 31 corresponding to a distance between the fulcrum 0 of the top panel 31 and the imaging position from the X-ray CT image (step S101).

Then, the load estimation section 462A (FIG. 16) estimates a load L in an imaging position in imaging of the subject P by the step-and-shoot method based on the height h of the top panel 31 calculated by the top panel height calculation section 461 and a three-dimensional correction table (FIG. 5) stored in the correction data storage unit 45A (step S103A).

Specifically, the load estimation section 462A estimates a load L of the subject P applied to the top panel 31 based on the calculated height h of the top panel 31, the distance z between the fulcrum 0 of the top panel 31 and the imaging position of the subject P, and a correction table (FIG. 14) stored in the correction data storage unit 45A. In this case, since the load L of the subject P applied to the top panel 31 is constant (fixed value), the same value is obtained both by the helical scanning method and the step-and-shoot method.

Then, the correction amount estimation section 463A estimates the height h of the top panel 31 in an imaging range in imaging of the subject P by the step-and-shoot method based on the distance z between the fulcrum 0 of the top panel 31 and the imaging position in imaging of the subject P by the step-and-shoot method, the load L estimated by the load estimation section 462, and the three-dimensional correction table. In this case, the correction amount estimation section 463A calculates an imaging range in imaging of the subject P by the step-and-shoot method from the distance z, reads the three-dimensional correction table, and estimates the height h of the top panel 31 corresponding to the load L in the imaging range (step S105A).

Then, the correction image generation section 464A calculates a correction amount (top panel sagging correction amount) for correcting the height of the top panel 31 of the captured PET image to the estimated height of the PET image (height of the X-ray CT image) based on the height h of the top panel 31 estimated by the correction amount estimation section 463A (step S107A). The correction image generation section 464A stores the calculated top panel sagging correction amount in the correction data storage unit 45A.

As described above, in the PET-CT apparatus according to the second embodiment, the correction unit 46A estimates the load L and the height h of the top panel in the imaging position in imaging by the step-and-shoot method based on the height h of the top panel 31 imaged by the helical scanning method and the three-dimensional correction table, and corrects the PET image captured by the step-and-shoot method.

Thus, in the PET-CT apparatus according to the second embodiment, the correction unit 46A can fuse the corrected PET image and X-ray CT image, thereby allowing correction with high accuracy and generation of a fusion image.

In the PET-CT apparatus according to the second embodiment, the PET frame device 1 is used to generate the PET image, but as in the first embodiment, for example, a SPECT apparatus may be used.

When the CT frame device 2 images the subject P by the step-and-shoot method, the top panel 31 of the bed device 3 is imaged. Thus, the load L in the imaging position (imaging central position) may be estimated from a distance z between the imaged top panel 31 and the imaging position and the height h of the imaged top panel 31 by referring to the three-dimensional correction table.

Third Embodiment

In the first and second embodiments described above, in the PET-CT apparatus, the PET frame device 1 performs imaging by the step-and-shoot method, but this embodiment is not limited to this.

Specifically, instead of the PET frame device 1, a magnetic resonance imaging apparatus may be used that applies a magnetic field to a human body and uses a magnetic resonance phenomenon of hydrogen nucleus in the body. Specifically, the present invention may be applied to modality with a plurality of imaging methods using the CT frame device 2 for imaging by the helical scanning method, and a magnetic resonance apparatus.

Although a couple of embodiments of the invention are explained, these embodiments are exemplary only and it is not intended that the scope of the invention is limited by the embodiments. These embodiments can be put into practice in other various forms, and can be variously omitted, replaced or changed within the scope of the invention. The embodiments and their modifications are included in the scope and the coverage of the invention, and similarly in the equivalents to the claimed invention.

Also, in the embodiments of the present invention, the steps of flow charts show example processes that are performed in time-series in the order described, but they may also include processes that can be performed in parallel or independently rather than being performed in time-series.

What is claimed is:

1. A diagnostic imaging apparatus comprising:
   a top panel height calculation unit configured to calculate a height of a top panel corresponding to the distance between the fulcrum of the top panel and the imaging position, from an image captured by continuous imaging of the subject;
   an imaging position estimation unit configured to estimate an imaging position of an image captured by a different imaging method from a method for the captured image based on the height of the top panel calculated by the top panel height calculation unit, the distance between the fulcrum of the top panel corresponding to the height and the imaging position, and a correction table, the correction table being a table in which a protrusion amount of a top panel and a bending amount of the top panel corresponding to the protrusion amount are associated, or a distance between a fulcrum of the top panel and an imaging position of a subject, and a height of the top panel in the imaging position are associated; and
   an image correction unit configured to align the imaging position of the image captured by the different imaging method with the imaging position of the image captured by the continuous imaging.

2. The diagnostic imaging apparatus according to claim 1, further comprising:
   a first captured image correction section configured to correct a difference between the height of the top panel calculated by the top panel height calculation unit and a height of the top panel defined by a top panel reference profile, the top panel reference profile indicating a reference position of the top panel,
   wherein the correction table is such that the protrusion amount, a bending amount of the top panel corresponding to the protrusion amount, and a tilt of the top panel are associated,
   the imaging position estimation unit includes a top panel tilt estimation section configured to consider the difference in the height of the top panel as the bending amount of the top panel based on the protrusion amount in the imaging position in continuous imaging of the subject, the difference in the height of the top panel, and the correction table, and estimate the tilt of the top panel in the imaging position in imaging by the different imaging method, and
   a top panel position calculation section configured to calculate the top panel position in the imaging position in imaging by the different imaging method from the estimated tilt of the top panel, and
   the image correction unit includes a second captured image correction section configured to correct the calculated top panel position to the height of the top panel defined by the top panel reference profile.

3. The diagnostic imaging apparatus according to claim 2, further comprising an image fusion section configured to fuse a first captured image corrected by the first captured image correction section, and a second captured image corrected by the second captured image correction section.

4. The diagnostic imaging apparatus according to claim 2, wherein the top panel reference profile is measurement information obtained by imaging a range that can be imaged by a helical scanning method with the subject being not placed on the top panel, and previously measuring the bending amount of the top panel.

5. The diagnostic imaging apparatus according to claim 2, wherein the imaging method for continuously imaging the subject is a helical scanning method, and the imaging method for imaging by the different imaging method is a step-and-shoot method for discretely imaging the subject.

6. The diagnostic imaging apparatus according to claim 5, wherein the imaging method for continuously imaging the subject is performed by an X-ray CT apparatus, and
the imaging method for imaging by the different imaging method is performed by a PET device.

7. The diagnostic imaging apparatus according to claim 1, wherein the correction table is such that the distance between the fulcrum of the top panel and the imaging position of the subject, the height of the top panel in the imaging position, and a load of the subject applied to the top panel are associated,
the imaging position estimation unit includes a load estimation section configured to estimate the load based on the height of the top panel calculated by the top panel height calculation unit, the distance between the fulcrum of the top panel and the imaging position of the subject, and the correction table, and
a correction amount estimation section configured to estimate a height of the top panel in an imaging range in imaging of the subject by the different imaging method based on the distance between the fulcrum of the top panel and the imaging position in imaging by the different imaging method, the estimated load, and the correction table, and
the image correction unit includes a correction image generation section configured to correct the image captured by the different imaging method to the estimated height of the top panel, and generate a captured image with the height of the top panel being corrected.

8. The diagnostic imaging apparatus according to claim 7, further comprising an image fusion section configured to fuse the captured image corrected by the different imaging method, and the image captured by continuous imaging.

9. The diagnostic imaging apparatus according to claim 7, wherein the imaging method for continuously imaging the subject is the helical scanning method, and
the imaging method for imaging by the different imaging method is a step-and-shoot method for discretely imaging the subject.

10. The diagnostic imaging apparatus according to claim 9, wherein the imaging method for continuously imaging the subject is performed by a X-ray CT apparatus, and
the imaging method for imaging by the different imaging method is performed by a PET device.

11. A control method of a diagnostic imaging apparatus including a top panel reference profile indicating a reference position of a top panel, and a correction table in which a protrusion amount of the top panel, a bending amount of the top panel corresponding to the protrusion amount, and a tilt of the top panel are associated, comprising:
a top panel height calculation step of calculating a height of the top panel corresponding to a distance between a fulcrum of the top panel and an imaging position, from an image captured by continuous imaging of a subject;
a top panel tilt estimation step of considering a difference in the height of the top panel as the bending amount of the top panel based on a protrusion amount in the imaging position in continuous imaging of the subject, the difference in the height of the top panel, and the correction table, and estimating the tilt of the top panel in an imaging position in imaging by a different imaging method;
a top panel position calculation step of calculating a top panel position in the imaging position in imaging by the different imaging method from the estimated tilt of the top panel, and
a captured image correction step of correcting the calculated top panel position to the height of the top panel defined by the top panel reference profile.

12. A control method of a diagnostic imaging apparatus including a correction table in which a distance between a fulcrum of a top panel and an imaging position of a subject, a height of the top panel in the imaging position, and a load of the subject applied to the top panel are associated, comprising:
a top panel height calculation step of calculating the height of the top panel corresponding to a distance between the fulcrum of the top panel and the imaging position, from an image captured by continuous imaging of the subject;
a load estimation step of estimating the load based on the height of the top panel calculated by the top panel height calculation step, the distance between the fulcrum of the top panel and the imaging position of the subject, and the correction table;
a correction amount estimation step of estimating a height of the top panel in an imaging range in imaging of the subject by a different imaging method based on the distance between the fulcrum of the top panel and the imaging position in imaging by the different imaging method, the estimated load, and the correction table; and
a correction image generation step of correcting the image captured by the different imaging method to the estimated height of the top panel, and generating a captured image with the height of the top panel being corrected.

* * * * *

UNITED STATES PATENT AND TRADEMARK OFFICE
CERTIFICATE OF CORRECTION

Page 1 of 1

PATENT NO. : 9,504,437 B2
APPLICATION NO. : 14/332477
DATED : November 29, 2016
INVENTOR(S) : Yasuhiro Noshi et al.

It is certified that error appears in the above-identified patent and that said Letters Patent is hereby corrected as shown below:

On the Title Page

Item (63), the Related U.S. Application Data information has been omitted. Item (63) should read:

--Related U.S. Application Data
(63) Continuation of Application PCT/JP2013/066882,
Filed on Jun. 19, 2013--

Signed and Sealed this
Tenth Day of July, 2018

Andrei Iancu
*Director of the United States Patent and Trademark Office*